(12) United States Patent
Harmon

(10) Patent No.: US 8,741,638 B2
(45) Date of Patent: Jun. 3, 2014

(54) IN VITRO EXPANSION OF POSTPARTUM-DERIVED CELLS IN ROLLER BOTTLES

(75) Inventor: Alexander M. Harmon, Clinton, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 620 days.

(21) Appl. No.: 11/612,872

(22) Filed: Dec. 19, 2006

(65) Prior Publication Data

US 2007/0141700 A1 Jun. 21, 2007

Related U.S. Application Data

(60) Provisional application No. 60/751,550, filed on Dec. 19, 2005.

(51) Int. Cl.
*C12N 5/02* (2006.01)
*C12N 5/07* (2010.01)

(52) U.S. Cl.
USPC .......................... 435/366; 435/325; 435/372

(58) Field of Classification Search
None
See application file for complete search history.

(56) References Cited

U.S. PATENT DOCUMENTS

| | | | |
|---|---|---|---|
| 4,352,883 A | 10/1982 | Lim | |
| 4,882,162 A | 11/1989 | Ikada et al. | |
| 4,963,489 A | 10/1990 | Naughton et al. | |
| 5,004,681 A | 4/1991 | Boyse et al. | |
| 5,192,553 A | 3/1993 | Boyse et al. | |
| 5,266,476 A * | 11/1993 | Sussman et al. | 435/399 |
| 5,286,632 A | 2/1994 | Jones | |
| 5,320,962 A | 6/1994 | Stiles et al. | |
| 5,342,761 A | 8/1994 | MacLeod | |
| 5,437,994 A | 8/1995 | Emerson et al. | |
| 5,443,950 A | 8/1995 | Naughton et al. | |
| 5,456,835 A | 10/1995 | Castino et al. | |
| 5,460,939 A | 10/1995 | Hansbrough et al. | |
| 5,486,359 A | 1/1996 | Caplan et al. | |
| 5,580,777 A | 12/1996 | Bernard et al. | |
| 5,589,376 A | 12/1996 | Anderson et al. | |
| 5,670,483 A | 9/1997 | Zhang et al. | |
| 5,677,181 A | 10/1997 | Parish | |
| 5,730,933 A | 3/1998 | Peterson | |

(Continued)

FOREIGN PATENT DOCUMENTS

EP 0 333 328 9/1989
EP 0 552 380 7/1993

(Continued)

OTHER PUBLICATIONS

Melero-Martin, J. M. et al., "Optimal In-Vitro Expansion of Chondroprogenitor Cells in Monlayer Culture," *Biotechnology and Bioengineering*, Feb. 2006, 93(3), 519-533.

(Continued)

*Primary Examiner* — Catherine Hibbert
(74) *Attorney, Agent, or Firm* — Bernard F. Plantz; Johnson & Johnson

(57) ABSTRACT

Methods for the maximizing parameter of the in vitro growth and expansion of mammalian cells, specifically postpartum-derived cells in containers such as roller bottles is described. Methods of optimizing growth rate and cell yield in such culture systems are provided. The methods are particularly adapted for human postpartum-derived cells, such as umbilicus-derived cells.

6 Claims, 5 Drawing Sheets

(56) References Cited

U.S. PATENT DOCUMENTS

| | | |
|---|---|---|
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,869,079 A | 2/1999 | Wong et al. |
| 5,902,741 A | 5/1999 | Purchio et al. |
| 5,906,934 A | 5/1999 | Grande et al. |
| 5,919,702 A | 7/1999 | Purchio et al. |
| 5,942,225 A | 8/1999 | Bruder et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,153,591 A | 11/2000 | Cai et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,372,494 B1 | 4/2002 | Naughton et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,497,875 B1 | 12/2002 | Sorrell et al. |
| 6,528,245 B2 | 3/2003 | Sanchez-Ramos et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,524,489 B2 | 4/2009 | Messina et al. |
| 7,560,276 B2 | 7/2009 | Harmon et al. |
| 8,277,796 B2 | 10/2012 | Messina et al. |
| 8,318,483 B2 | 11/2012 | Mistry et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0235563 A1 | 12/2003 | Strom et al. |
| 2003/0235909 A1 | 12/2003 | Hariri et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0101958 A1 | 5/2004 | Shimp |
| 2004/0136967 A1 | 7/2004 | Weiss et al. |
| 2005/0019865 A1 | 1/2005 | Kihm et al. ............... 435/69.1 |
| 2005/0032209 A1 | 2/2005 | Messina et al. |
| 2005/0037491 A1 | 2/2005 | Mistry et al. |
| 2005/0054098 A1 | 3/2005 | Mistry et al. ............... 424/93.7 |
| 2005/0058629 A1 | 3/2005 | Harmon et al. |
| 2005/0058630 A1 | 3/2005 | Harris et al. |
| 2005/0058631 A1 | 3/2005 | Kihm et al. ............... 435/325 |
| 2005/0074435 A1 | 4/2005 | Casper et al. |
| 2005/0148074 A1 | 7/2005 | Davies et al. |
| 2005/0249731 A1 | 11/2005 | Aslan et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. ............... 435/325 |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0275362 A1 | 11/2007 | Edinger et al. |
| 2008/0112939 A1 | 5/2008 | Colter et al. |
| 2008/0145934 A1 | 6/2008 | Harris et al. |

(56) References Cited

U.S. PATENT DOCUMENTS

| | | | |
|---|---|---|---|
| 2008/0166328 | A1 | 7/2008 | Harmon et al. |
| 2010/0210013 | A1 | 8/2010 | Mistry et al. |
| 2010/0215714 | A1 | 8/2010 | Messina et al. |
| 2010/0260843 | A1 | 10/2010 | Messina et al. |
| 2012/0315251 | A1 | 12/2012 | Harris et al. |
| 2013/0022585 | A1 | 1/2013 | Messina et al. |

FOREIGN PATENT DOCUMENTS

| | | |
|---|---|---|
| EP | 1 216 718 | 6/2002 |
| JP | 2003-235549 | 8/2003 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 96/01316 | 1/1996 |
| WO | WO 96/05309 | 2/1996 |
| WO | WO 98/17791 | 4/1998 |
| WO | WO 98/33515 | 8/1998 |
| WO | WO 98/51317 | 11/1998 |
| WO | WO 99/03973 | 1/1999 |
| WO | WO 99/28444 | 6/1999 |
| WO | WO 00/09666 | 2/2000 |
| WO | WO 00/38762 | 7/2000 |
| WO | WO 00/46351 | 8/2000 |
| WO | WO 01/11011 | 2/2001 |
| WO | WO 01/19379 | 3/2001 |
| WO | WO 01/34775 | 5/2001 |
| WO | WO 02/36751 | 5/2002 |
| WO | WO 02/46373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/054146 | 7/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070749 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2004/072273 | 8/2004 |
| WO | 2005/001078 A2 | 1/2005 |
| WO | WO 2005/001076 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/021738 | 3/2005 |
| WO | WO 2005/038012 | 4/2005 |
| WO | WO 2005/042703 | 5/2005 |
| WO | WO 2006/036826 | 4/2006 |
| WO | WO 2006/071773 | 7/2006 |
| WO | WO 2006/071777 | 7/2006 |
| WO | WO 2006/071778 | 7/2006 |
| WO | WO 2006/071794 | 7/2006 |
| WO | WO 2006/071802 | 7/2006 |
| WO | WO 2006/083394 | 8/2006 |
| WO | WO 2006/105152 | 10/2006 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |
| WO | WO 2007/073552 R | 6/2008 |

OTHER PUBLICATIONS

Ulloa-Montoya, F. et al., "Culture Systems for Pluripotent Stem Cells," *Journal of Bioscience and Bioengineering*, 2005, 100(1), 12-27.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.

(56) References Cited

OTHER PUBLICATIONS

In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the United States Patent and Trademark Office, Final Office Action in re: U.S. Appl. No. 11/315,898, dated Sep. 16, 2008, 19 pages.
In the United States Patent and Trademark Office, Non-Final Office Action in re: U.S. Appl. No. 11/323,372, dated Sep. 3, 2008, 45 pages.
In the United States Patent and Trademark Office, Non-Final Office Action in re: U.S. Appl. No. 11/317,574, dated Sep. 30, 2008, 26 pages.
In the United States Patent and Trademark Office, Non-Final Office Action in re: U.S. Appl. No. 11/315,969, dated Dec. 23, 2008, 18 pages.
In the U. S. Patent and Trademark Office, Non-Final Office Action in re: U.S. Appl. No. 11/321,864, dated Jan. 8, 2009, 34 pages.
In the U. S. Patent and Trademark Office, Non-Final Office Action in re: U.S. Appl. No. 11/315,943, dated Feb. 20, 2009, 17 pages.
In the U. S. Patent and Trademark Office, Non-Final Office Action in re: U.S. Appl. No. 11/297,778, dated Mar. 9, 2009, 12 pages.
In the U. S. Patent and Trademark Office, Non-Final Office Action in re: U.S. Appl. No. 10/877,445, dated Mar. 19, 2009, 23 pages.
In the U. S. Patent and Trademark Office, Non-Final Office Action in re: U.S. Appl. No. 11/481,481, dated Mar. 20, 2009, 48 pages.
In the U. S. Patent and Trademark Office, Final Office Action in re: U.S. Appl. No. 11/315,897, dated Mar. 20, 2009, 21 pages.
In the U. S. Patent and Trademark Office, Non-Final Office Action in re: U.S. Appl. No. 11/481,480, dated Mar. 20, 2009, 50 pages.
In the U. S. Patent and Trademark Office, Final Office Action in re: U.S. Appl. No. 11/321,863, dated Feb. 12, 2009, 24 pages.
In the U. S. Patent and Trademark Office, Final Office Action in re: U.S. Appl. No. 11/322,003 dated Feb. 13, 2009, 24 pages.
In the U. S. Patent and Trademark Office, Final Office Action in re: U.S. Appl. No. 10/876,998 dated Feb. 13, 2009, 18 pages.
In the U. S. Patent and Trademark Office, Final Office Action in re: U.S. Appl. No. 11/322,372 dated Feb. 13, 2009, 22 pages.
In the U. S. Patent and Trademark Office, Non-Final Office Action in re: U.S. Appl. No. 11/481,456 dated Apr. 16, 2009, 50 pages.
In the U. S. Patent and Trademark Office, Non-Final Office Action in re: U.S. Appl. No. 11/317,574 dated Apr. 29, 2009, 29 pages.
In the U. S. Patent and Trademark Office, Non-Final Office Action in re: U.S. Appl. No. 11/817,045 dated Apr. 27, 2009, 12 pages.
In the U. S. Patent and Trademark Office, Advisory Action in re: U.S. Appl. No. 11/322,372 dated May 13, 2009, 7 pages.
In the U. S. Patent and Trademark Office, Advisory Action in re: U.S. Appl. No. 11/322,372 dated May 12, 2009, 13 pages.
In the U. S. Patent and Trademark Office, NonFinal Office Action in re: U.S. Appl. No. 10/877,446 dated Jun. 12, 2009, 16 pages.
Abbas, A.K. et al., *Cellular and Molecular Immunology*, 5th Ed. (2003) Saunders, Philadelphia, p. 171.
Agbulut, O. et al., "Comparison of Human Skeletal Myoblasts and Bone Marrow-Derived CD133$^+$ Progenitors for the Repair of Infarcted Myocardium," *Journal of the American College of Cardiology*, 2004; 44(2):458-63.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-08.
Altman, G.H. et al., "Advanced Bioreactor With Controlled Application of Multi-Dimensional Strain for Tissue Engineering," *J. Biomech. Eng.*, 2002; 124:742-49.
Altman R.D. et al., "Radiographic Assessment of Progression in Osteoarthritis," *Arthritis & Rheum.*, 1987; 30(11):1214-25.
Auda-Boucher, G. et al., "Staging of the Commitment of Murine Cardiac Cell Progenitors," *Dev. Bio.*, 2000; 225(1):214-25.
Avital, I. et al., "Isolation, Characterization, and Transplantation of Bone Marrow-Derived Hepatocyte Stem Cells," *Biochem. & Biophys. Res. Comm.*, 2001; 288:156-64.
Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-13.
Bao, Z.Z. et al., "Regulation of Chamber-Specific Gene Expression in the Developing Heart by IrX 4," *Science*, 1999; 283(5405):1161-64 (Abstract 1 page).
Barberi, T. et al., "Neural Subtype Specification of Fertilization and Nuclear Transfer Embryonic Stem Cells and Application in Parkinsonian Mice," *Nature Biotechnology*, 2003; 21(10):1200-07.
Beck, R.W. et al., "A Clinical Comparison of Visual Field Testing With a New Automated Perimeter, The Humphrey Field Analyzer, and The Goldmann Perimeter," *Ophthalmology*, 1985; 92(1):77-82.
Bergers, G. et al., "The Role of Pericytes in Blood-Vessel Formation and Maintenance," *Neuro-Oncology*, 2005; 7:452-64.
Bhindi, R. et al., "Rat Models of Myocardial Infarction," *Thromb Haemost*, 2006; 96:602-10.
Brines, A. and Cerami, A., "Discovering erythropoietin's extra-hematopoietic functions: Biology and clinical promise," Kidney Int., 2006 70(2):246-250.
Brodsky, S.V., "Coagulation, Fibrinolysis and Angiogenesis: New Insights From Knockout Mice," *Exp. Nephrol.*, 2002;10:299-306.
Brown, J.A. et al., "Blockade of Programmed Death-1 Ligands on Dendritic Cells Enhances T Cell Activation and Cytokine Production," *J. Immunology*, 2003; 170:1257-1266.
Caballero, S. et al., "The Many Possible Roles of Stem Cells in Age-Related Macular Degeneration," *Graefe's Arch. Clin. Exp. Ophthalmol.*, 2004; 242:85-90.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-46.
Cao, Q. et al., "Stem Cell Repair of Central Nervous System Injury," *J. of Neuroscience Res.*, 2002; 68:501-10.
Caplan, A.I. et al., "Mesenchymal Stem Cells: Building Blocks for Molecular Medicine in the 21st Century," *Trends in Molecular Med.*, 2001; 7(6):259-64.
Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.
Chagraoui, J. et al., "Fetal Liver Stroma Consists of Cells in Epithelial-to-Mesenchymal Transition," *Blood*, 2003; 101(8):2973-2982.
Chen, D., et al, "Differential Roles for Bone Morphogenic Protein (BMP) Receptor Type IB and IA in Differentiation and Specification

(56) References Cited

OTHER PUBLICATIONS of Mesenchymal Precursor Cells to Osteoblast and Adipocyte Lineages," *J. Cell Biol.*, 1998; 142(1):295-305.
Chen, H. et al., "The Effect of Hypothermia on Transient Middle Cerebral Artery Occlusion in the Rat," *J. Cereb. Blood Flow Metab.*, 1992; 12(4):621-628.
Chen J. et al., "Therapeutic Benefit of Intravenous Administration of Bone Marrow Stromal Cells after Cerebral Ischernia in Rats," *Stroke*, 2001; 32(4):1005-1011.
Chong, Z.Z., et al., "Erythropoietin Is a Novel Vascular Protectant Through Activation of Akt1 and Mitochondrial Modulation of Cysteine Proteases," Circulation, 2002;106 (23): 2973-2979.
Constantini, S. et al., "The Effects of Methylprednisolone and the Ganglioside GM1 on Acute Spinal Cord Injury in Rats," *J. Neurosurg.*, 1994; 80(1):97-111.
Coumans, B. et al., "Lymphoid Cell Apoptosis Induced by Trophoblastic Cells: A Model of Active Foeto-Placental Tolerance," *J. of Immunological Methods*, 1999; 224:185-196.
D'Cruz, P.M. et al., "Mutation of the Receptor Tyrosine Kinase Gene Mertk in the Retinal Dystrophic RCS Rat," *Hum. Mol. Genet.*, 2000; 9(4):645-651.
Daley, G.Q. et al., "Realistic Prospects for Stem Cell Therapeutics," *Hematol.*, 2003; 398-418.
Davies, S.M. et al., "Engraftment and Survival After Unrelated-Donor Bone Marrow Transplantation: A Report From The National Marrow Donor Program," *Blood*, 2000; 96(13):4096-4102.
del Monte, F. et al., "Improvement in Survival and Cardiac Metabolism After Gene Transfer of Sarcoplasmic Reticulum $Ca^{2+}$—ATPase in a Rat Model of Heart Failure," *Circulation*, 2001;104:1424-1429.
Dickinson, A.M. et al., "Non-HLA Immunogenetics in Hematopoietic Stem Cell Transplantation," *Curr. Opin. Immunol.*, 2005; 17(5):517-525.
Dimri, G.P. et al., "A Biomarker That Identifies Senescent Human Cells in Culture and in Aging Skin in Vivo," *Proc. Natl. Acad. Sci. USA*, 1995; 92:9363-67.
Doshi, S.N. et al., "Evolving Role of Tissue Factor and Its Pathway Inhibitor," *Critical Care Med.*, 2002; 30(5):S241-50.
Doyle, J., "Spiraling Complexity, Robustness, and Fragility in Biology," http://www.cds.caltech.edu/~doyle/CmplxNets/Bio1.pdf, available online Feb. 28, 2004.
Eagle, H., "The Specific Amino Acid Requirements of a Mammalian Cell (Strain L) in Tissue Culture," *J. Biol. Chem.*, 1955; 214(2):839-52.
Eblenkamp, M. et al., "Umbilical Cord Stromal Cells (UCSC). Cells Featuring Osteogenic Differentiation Potential," *Der Orthopade*, Dec. 2004; 33:1338-45 (English abstract on p. 1339), abstract only.
Edelstein, M. L. et al., "Gene Therapy Clinical Trials Worldwide 1989-2004—An Overview," *J. Gene Med.*, 2004; 6(6):597-602.
Edlund, H., "Pancreatic Organogenesis—Developmental Mechanisms and Implications for Therapy," *Nat. Rev. Genet.*, 2002; 3:524-32.
Efrat, S. et al., "Cell Replacement Therapy for Type 1 Diabetes," *Trends in Molecular Medicine*, 2002; 8(7):334-39.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-74.
Ehtesham, M. et al., "The Use of Interleukin 12-Secreting Neural Stem Cells for the Treatment of Intracranial Glioma," *Cancer Res.*, 2002; 5657-63.
Eisenhofer, G.E. et al., "Tyrosinase: A Developmentally Specific Major Determinant of Peripheral Dopamine," *FASEB J.*, 2003; 17: 1248-55.
Erices et al., 'Mesenchymal Progenitor Cells in Human Umbilical Cord Blood, *Br. J. Haematol.*, 2000; 109(1):235-242.
Fazleabas, A.T. et al., "Endometrial Function: Cell Specific Changes in the Uterine Environment," *Mol. & Cellular. Endo.*, 2002; 186:143-147.

Fernandes, A.M. et al., "Mouse Embryonic Stem Cell Expansion in a Microcarrier-based Stirred Culture System," *Journal of Biotechnology*, 2007; 132(2): 227-236.
Fiegel, H.C. et al., "Liver-Specific Gene Expression in Cultured Human Hematopoietic Stem Cells," *Stem Cells*, 2003;21:98-104.
Fischer, D. et al., "Lens-Injury-Stimulated Axonal Regeneration Throughout the Optic Pathway of Adult Rats," *Exp. Neurol.*, 2001; 172:257-272.
Foley, A. et al., "Heart Induction: Embryology to Cardiomyocyte Regeneration," *Trends Cardiovasc. Med.*, 2004; 14(3):121-25.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-19.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Fukuchi, Y. et al., "Human Placenta-Derived Cells Have Mesenchymal Stem/Progenitor Cell Potential," *Stem Cells*, 2004; 22(5):649-58.
Fukuda, K., "Reprogramming of Bone Marrow Mesenchymal Stem Cells Into Cardiomyocytes," *C.R. Biol.*, 2002; 325:1027-1038.
Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Gökhan, S. et al., "Basic and Clinical Neuroscience Applications of Embryonic Stem Cells," *Anat. Rec. (New Anat)*, 2001; 265:142-56.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001: 7;581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.
Gottleib, D.I. "Large-Scale Sources of Neural Stem Cells," *Annu. Rev. Neurosci.*, 2002; 25:381-407.
Gröhn, P. et al., "Collagen-Coated $BA^{2+}$-Alginate Microcarriers for the Culture of Anchorage-Dependent Mammalian Cells," *BioTechniques*, 1997; 22(5): 970-975.
Gupta, S. et al., "Isolation and Characterization of Kidney-Derived Stem Cells," *J. of Am. Soci. of Nephrol.*, 2006; 17(11):3028-40.
Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-25.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Herrera, M.B. et al., "Mesenchymal Stem Cells Contribute to the Renal Repair of Acute Tubular Epithelial Injury," *Int. J. Mol. Med.*, 2004; 14(6):1035-41.
Hill, D.P. et al., "Screening for Novel Pattern Formation Genes Using Gene Trap Approaches," *Methods in Enzymology*, 1993; 225:664-81.
Hill, M. et al., "Treatment for Swallowing Difficulties (Dysphagia) in Chronic Muscle Disease," *The Cochrane Library Cochrane Database Syst Rev.*, 2004; 2:1-12.
Hishikawa, K. et al., "Musculin/MyoR is Expressed in Kidney Side Population Cells and Can Regulate Their Function," *Journal of Cell Biology*, 2005; 169(6):921-28.
Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.
Hoynowski, S.M. et al., "Characterization and Differentiation of Equine Umbilical Cord—Derived Matrix Cells," *Biochemical and Biophysical Research Communications*, 2007; 362:347-53.
Hu, A. et al., "Hepatic Differentiation From Embryonic Stem Cells In Vitro," *Chin. Med. J.*, 2003; 116(12):1893-97.

(56) References Cited

OTHER PUBLICATIONS

Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.

In't Anker, P., et al., "Isolation of Mesenchymal Stern Cells of Fetal or Maternal Origin from Human Placenta," *Stem Cells*, 2004; 22:1338-45.

Ishii, M. et al.,"Molecular Markers Distinguish Bone Marrow Mesenchymal Stem Cells From Fibroblasts," *Biochemical and Biophysical Research Communications*, Jun. 24, 2005; 332(1):297-303.

Ito, Y. et al., "A Quantitative Assay Using Basement Membrane Ex tracts to Study Tumor Angiogenesis In Vivo," *Int. J. Cancer*, 1996; 67:148-152.

Jaffe, E.A. et al., "Culture of Human Endothelial Cells Derived From Umbilical Veins; Identification by Morphologic and Immunologic Criteria" *J Clin Invest*, 1973; 52:2745-56.

Janderová, L. et al., "Human Mesenchymal Stem Cells as an In Vitro Model for Human Adipogenesis," *Obes. Res.*, 2003; 11(1):65-74.

Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75:573-584.

Johe, K.K. et al., "Single Factors Direct the Differentiation of Stem Cells From the Fetal and Adult Central Nervous System," *Genes & Devel.*, 1996;10:3129-3140.

Johnstone, B. et al., "In Vitro Chondrogenesis of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Jones, J. et al., "Insulin-Like Growth Factors and their Binding Proteins: Biological Actions," *Endocrine Review*, 1995; 16(1):3-34.

Jones-Villeneuve, E.M. et al., "Retinoic Acid-Induced Neural Differentiation of Embryonal Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.

Kadiyala, S. et al., "Culture Expanded Canine Mesenchymal Stem Cells Possess Osteochondrogenic Potential In Vivo and In Vitro," *Cell Transplant.*, 1997; 6(2):125-134.

Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, Sep. 1984; 160:633-51.

Kirschstein, R. et al., "Can Stem Cells Repair a Damaged Heart?" *Stem Cells: Scientific Progress and Future Research Directions*, 2001; 87-92.

Kitamura, S. et al., "Establishment and Characterization of Renal Progenitor Like Cells from S3 Segment of Nephron in Rat Adult Kidney," *The FASEB Journal: Official Publication of The Federation of American Societies for Experimental Biology*, 2005; 19(13)1789-97.

Klein, J., *Immunology: The Science of Self-Nonself Discrimination*, (1982) John Wiley & Sons, New York, 453-58.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.

Kushida, A., et al., "Decrease in Culture Temperature Releases Monolayer Endothelial Cell Sheets Together with Deposited Fibronectin Matrix from Temperature-Responsive Culture Surfaces," *J. of Biomedical Materials Research*, 1999; 45(4):355-362.

Laface, D. et al., "Gene Transfer Into Hematopoietic Progenitor Cells Mediated by an Adeno-Associated Virus Vector," *Virology*, 1998; 162:483-86.

Lang, K.J.D. et al., "Differentiation of Embryonic Stem Cells to a Neural Fate: A Route to Re-Building the Nervous System?" *J. of Neurosci. Res.*, 2004; 76:184-92.

Langeggen, H. et al., "HUVEC Take Up Opsonized Zymosan Particles and Secrete Cytokines IL-6 and IL-8 In Vitro," *FEMS Immunol. Med. Microbiol.*, 2003; 36:55-61.

Le Belle, J.E. et al., "Stem Cells for Neurodegenerative Disorders: Where Can We Go From Here?," Biodrugs, 2002; 16(6):389-401.

Le Bouteiller, P. et al., "Soluble HLA-G1 at the Materno-Foetal Interface-A Review," *Placenta*, 2003; 24 (Suppl. A):S10-S15.

Li, A. et al., "IL-8 Directly Enhanced Endothelial Cell Survival, Proliferation, and Matrix Metalloproteinases Production and Regulated Angiogenesis," *J. Immunol.*, 2003; 170(6):3369-3376.

Li, C.D. et al., "Mesenchymal Stem Cells Derived From Human Placenta Suppress Allogeneic Umbilical Cord Blood Lymphocyte Proliferation," *Cell Research*, 2005; 15(7):539-47.

Li, Y. et al., "Transplanted Olfactory Ensheathing Cells Promote Regeneration of Cut Adult at Optic Nerve Axons," *J. of Neuro.*, 2003; 23(21):7783-7788.

Liddiard, et al., "An Improved Method for the Preparation of Human Fetal and Adult Hepatocytes," *Arch. Toxicol.*, 1980; 44(1-3):107-112.

Lindvall, O. et al., "Stem Cell Therapy for Human Neurodegenerative Disorders—How to Make It Work," *Nature Medicine*, 2004;10(Suppl.):S42-S50.

Lockhart, D.J. et al., "Expression Monitoring by Hybridization to High-Density Oligonucleotide Arrays," *Nat. Biotechnol.*, 1996;14(13):1675-80.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-51.

Luo, D. et al., "Synthetic DNA Delivery Systems," *Nat. Biotechnol.*, 2000; 18(1):33-36.

Luyten, F.P. et al., "Skeletal Tissue Engineering: Opportunities and Challenges," *Best Pract. Res. Clin. Rheumatol.*, 2001; 15(5):759-69.

Ma, L., et al., "Human Umbilical Cord Wharton's Jelly-Derived Mesenchymal Stem Cells Differntiation into Nerve-Like Cells," *Chinese Medical Journal*, 2005; 118(23):1, pp. 1987-1993.

MacDonald, R.J. "Expression of the Pancreatic Elastase I Gene in Transgenic Mice," *Hepatology*, 1987; 7(1):42S-51S.

MacKay, A.M. et al., "Chondrogenic Differentiation of Cultured Human Mesenchymal Stem Cells From Marrow," *Tissue Engineering*, 1998; 4(4):415-28.

Mason, A.J. et al., "The Hypogonadal Mouse: Reproductive Functions Restored by Gene Therapy," *Science*, 1986; 234:1372-1378.

Mayer-Proschel, M. et al., "Isolation of Lineage-Restricted Neuronal Precursors From Multipotent Neuroepithelial Stem Cells," *Neuron.*, 1997; 19:773-785.

McDonald, J.A. et al., "Diminished Responsiveness of Male Homosexual Chronic Hepatitis B Virus Carriers With HTLV-III Antibodies to Recombinant α-Interferon," *Hepatology*, 1987; 7(4):719-723.

Medicetty, S. et al., "Transplantation of Human Umbilical Cord Matrix Stem Cells Alleviates Apomorphine-Induced Rotations in Parkinsonian Rats", 2003, XP-002383776, 1 page.

Melero-Martin, J. et al., "Optimal In-Vitro Expansion of Chondroprogenitor Cells in Monolayer Culture," *Biotechnology and Bioengineering*, 2006; 93(3):519-33.

Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.

Mitchell, K.E. et al., "Matrix Cells From Wharton's Jelly Form Neurons and Glia," *Stem Cells*, 2003; 21:50-60.

Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-96.

(56) References Cited

OTHER PUBLICATIONS

Moulder, J.E., "Pharmacological Intervention to Prevent or Ameliorate Chronic Radiation Injuries," *Semin. Radiat. Oncol.*, 2003; 13(1):73-84.
Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," In Vitro *Cell Dev. Biol.*, 1990; 26(2):119-128.
Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70(1):121-29.
Nishishita, T. et al., "A Potential Pro-Angiogenic Cell Therapy With Human Placenta-Derived Mesenchymal Cells," *Biochemical and Biophysical Research Communications*, 2004; 325:24-31.
Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279(2):500-04.
Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.
Orlic, D. et al., "Stem Cells for Myocardial Regeneration," *Circ. Res.*, 2002; 91:1092-1102.
Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.
Palù, G. et al., "In Pursuit of New Developments for Gene Therapy of Human Diseases," *J. Biotechnol.*, Feb. 1999; 68(1):1-13.
Panepucci, R.A. et al., "Comparison of Gene Expression of Umbilical Cord Vein and Bone Marrow-Derived Mesenchymal Stem Cells," *Stem Cells*, 2004; 22(7):1263-78.
Pera, M.F. et al., "Human Embryonic Stem Cells", *J. Cell Science*, 2000; 113:5-10.
Petersdorf, E.W., "HLA Matching in Allogeneic Stem Cell Transplantation," *Curr. Op. Hematol*, 2004; 11(6):386-391.
Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Multilineage Potential of Adult Human Mesenchymal Stern Cells," *Science*, 1999; 284:143-47 and seven pages of online supplementary material.
Pittenger, M.F. et al., "Mesenchymal Stem Cells and Their Potential as Cardiac Therapeutics," *Circ. Res.*, 2004; 95:9-20.
Plaia, T., et al., "Characterization of a New Nih-Registered Variant Human Embryonic Stem Cell Line, BG01V: A Tool for Human Embryonic Stem Cell Research," *Stem Cells*, 2006: 24(3): 531-546.
Pountos, I. et al., "Mesenchymal Stem Cell Tissue Engineering: Techniques for Isolation, Expansion and Application," *Injury*, 2007; 38(Supp. 4):S23-33.
Rabbany, S.Y. et al., "Molecular Pathways Regulating Mobilization of Marrow-Derived Stem Cells for Tissue Revascularization," *Trends in Molecular Med.*, 2003; 9(3):109-17.
Rafii, S. et al., "Therapeutic Stem and Progenitor Cell Transplantation for Organ Vascularization and Regeneration," *Nature Med.*, 2003; 9(6):702-12.
Rahman, Z. et al., "Isolation and Primary Culture Urothelial Cells from Normal Human Bladder," *Urol. Research*, 1987; 15:315-20.
Ramon-Cueto, A. et al., "Functional Recovery of Paraplegic Rats and Motor Axon Regeneration in Their Spinal Cords by Olfactory Ensheathing Glia," *Neuron*, 2000; 25:425-435.
Ratner, B.D., et al., "Biomaterials: Where We Have Been and Where we are Going," Annu. Rev. Biomed. Eng., 2004; 6:41-75.
Readhead, C. et al., "Expression of a Myelin Basic Protein Gene in Transgenic Shiverer Mice: Correction of the Dysmyelinating Phenotype," *Cell*, 1987; 48(4):703-712.

Rehman, J. et al., "Secretion of Angiogenic and Antiapoptotic Factors by Human Adipose Stromal Cells," *Circulation*, 2004; 109:1292-98.
Reubinoff, B.E. et al., "Neural Progenitors From Human Embryonic Stem Cells," *Nature Biotechnology*, 2001; 19:1134-40.
Reyes, M. et al., "Purification and Ex Vivo Expansion of Postnatal Human Marrow Mesodermal Progenitor Cells," *Blood*, 2001; 98(9):2615-25.
Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.
Rios, M. et al., "Catecholamine Synthesis is Mediated by Tyrosinase in the Absence of Tyrosine Hydroxylase," *J. Neurosci.*, 1999, 19(9): 3519-26.
Romanov, Y.A. et al., "Searching for Alternative Sources of Postnatal Human Mesenchymal Stem Cells," *Stem Cells*, 2003; 21:105-10.
Rosen, E.M. et al., "HGF/SF in Angiogenesis," *Ciba Found. Symp.*, 1997; 212:215-229.
Roskams, A.J. et al., "Directing Stem Cells and Progenitor Cells on the Stage of Spinal Cord Injury," *Exp. Neurol.*, 2005; 193:267-72.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2003; 7(1):11.
Sakariassen, K.S. et al., "Methods and Models to Evaluate Shear-Dependent and Surface Reactivity-Dependent Antithrombotic Efficacy," *Thromb. Res.*, 2001; 104:149-174.
Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, Aug. 2004; 4:743-65.
Sauve, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-38.
Schraermeyer, U. et al., "Subretinally Transplanted Embryonic Stem Cells Rescue Photoreceptor Cells From Degeneration in the RCS Rats," *Cell Transplantation*, 2001; 10:673-80.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.
Schwartz, R.E. et al., "Multipotent Adult Progenitor Cells From Bone Marrow Differentiate Into Functional Hepatocyte-Like Cells," *J. of Clin. Invest.*, 2002; 109(10):1291-1302.
Sebire, G. et al., "In Vitro Production of IL-6,IL-1 β, and Tumor Necrosis Factor-α by Human Embryonic Microglial and Neural Cells," *J. Immunol.*, 1993; 150(4):1517-23.
Sethe, S. et al., "Aging of Mesenchymal Stem Cells," *Ageing Research Reviews*, 2006; 5:91-116.
Shani, M., "Tissue-Specific Expression of Rat Myosin Light-Chain 2 Gene in Transgenic Mice," *Nature*, 1985; 314(6008):283-286.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-26.
Siminoff, R. et al., "Properties of Reptilian Cutaneous Mechanoreceptors," *Exp. Neurol.*, 1968; 20(3):403-14.
Song, H. et al., "Astroglia Induce Neurogenesis From Adult Neural Stem Cells," Nature, 2002; 417(6884):39-44.
Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12:355-364.
Street, C.N. et al., "Stem Cells: A Promising Source of Pancreatic Islets for Transplantation in Type 1 Diabetes," *Curr. Top Dev. Biol.*, 2003; 58:111-36.

(56) References Cited

OTHER PUBLICATIONS

Storch, T.G. "Oxygen Concentration Regulates 5-Azacytidine-Induced Myogenesis in $C_3H/10T1/2$ cultures," *Biochim. Biophys. Acta*, 1990; 1055:126-129.
Svendsen, C.N. et al., "Long-Term Survival of Human Central Nervous System Progenitor Cells Transplanted Into a Rat Model of Parkinson's Disease," *Experim. Neurol.*, 1997; 148:135-46.
Swanson, R.A. et al., "A Semiautomated Method for Measuring Brain Infarct Volume," *J. Cereb. Blood Flow Metab.*, 1990; 10(2):2902-93.
Swift, G. H. et al., "Tissue-Specific Expression of the Rat Pancreatic Elastase I Gene in Transgenic Mice," *Cell*, 1984; 38:639-646.
Taylor, D.A. et al., "Regenerating Functional Myocardium: Improved Performance After Skeletal Myoblast Transplantation," *Nature Medicine*, Aug. 1998; 4(8):929-33 (Erratum in *Nature Medicine*, 1998; 4(10):1200).
Thorsby, E. et al., "Role of HLA Molecules in the Induction of Alloimmune Responses: Clinical Significance in the Cyclosporine Era," *Transplant Proc.*, 2004; 36(Suppl 2S):16S-21S.
Timmermans, F. et al., "Stem Cells for the Heart, Are We There Yet?" *Cardiology*, 2003; 100(4):176-85.
Toma, C. et al., "Human Mesenchymal Stem Cells Differentiate to a Cardiomyocyte Phenotype in the Adult Murine Heart," Circulation 2002; 105:93-98.
Tomita, M. et al., "Bone Marrow-Derived Stem Cells Can Differentiate Into Retinal Cells in Injured Rat Retina," *Stem Cells*, 2002; 20:279-83.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001; 19:408-18.
Tresco, P.A. et al., "Cellular Transplants As Sources for Therapeutic Agents," *Advanced Drug Delivery Reviews*, 2000; 42:3-27.
Turner, D., "The Human Leucocyte Antigen (HLA) System," *Vox Sang.*, 2004; 87(Suppl 1):S87-S90.
Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-17.
Tusher, V.G. et al., "Significance Analysis of Microarrays Applied to the Ionizing Radiation Response," *PNAS*, 2001; 98(9):5116-5121.
Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
"Unigene Entry for Hs.522632, *Homo sapiens* TMP Metallopeptidase Inhibitor 1 (TIMP1)," printed from http://www.ncbi.nlm.nih.gov/UniGene on Oct. 12, 2006.
Urbich, C. et al., "Endothelial Progenitor Cells Characterization and Role in Vascular Biology,", *Circ. Res.*, 2004; 95:343-53.
Vajsar, J. et al., "Walker-Warburg syndrome," *Orphanet Journal of Rare Diseases*, 2006;1:29.
Van Hoffelen, S.J. et al., "Incorporation of Murine Brain Progenitor Cells Into the Developing Mammalian Retina," *Invest. Ophthalmol. Vis. Sci.*, 2003; 44(1):426-34.
Vassliopoulos, G. et al., "Transplanted Bone Marrow Regenerates Liver by Cell Fusion," *Nature*, 2003(6934); 422:901-04.
Verma, I. M. et al., "Gene Therapy—Promises, Problems and Prospects," *Nature*, Sep. 1997; 389(6648):239-42.
Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
von Koskull, H. et al., "Induction of Cytokeratin Expression in Human Mesenchymal Cells," *J. Cell Physiol.*, 1987; 133:321-29.
Walboomers, X .F. et al., "Cell and Tissue Behavior on Micro-Grooved Surfaces," *Odontology*, 2001; 89:2-11.
Wang, X . et al., "Cell Fusion Is the Principal Source of Bone-Marrow-Derived Hepatocytes," *Nature*, 2003; 422(6934):897-900.
Weiss, M.L. et al., "Transplantation of Porcine Umbilical Cord Matrix Cells Into the Rat Brain," *Exp. Neur.*, 2003; 182:288-99.
Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-92.
Wenning, G.K. et al., "Neural Transplantation in Animal Models of Multiple System Atrophy: A Review," *J. Nueral Transm.*, 1999; Suppl.(55):103-113.
Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29(6):1525-1539.
Wolford, L.M. et al., "Considerations in Nerve Repair," *BUMC Proceedings*, 2003; 16:152-156.
Woodbury, D., et al., "Adult Rat and Human Bone Marrow Stromal Cells Differentiate Into Neurons," *J. Neurosci. Res.*, 2000; 61(4):364-370.
Wulf, G.G. et al., "Mesengenic Progenitor Cells Derived From Human Placenta," *Tissue Engineering*, Larchmont, NY, Jul. 2004; 10(7/8):1136-47.
Xu, C. et al., "Characterization and Enrichment of Cardiomyocytes Derived From Human Embryonic Stem Cells," *Circ. Res.*, 2002; 91(5):501-508.
Xu, Y. et al., "Dopamine, in the Presence of Tyrosinase, Covalently Modifies and Inactivates Tyrosine Hydroxylase," *J. Neurosci. Res.*, 1998; 54(5):691-97.
Yamashima, T., "Implication of Cysteine Proteases Calpain, Cathepsin and Caspase in Ischemic Neuronal Death of Primates," *Progress in Neurobiology*, 2000; 62:273-295.
Yang, C. et al., "Enhancement of Neovascularization With Cord Blood $CD133^+$ Cell-Derived Endothelial Progenitor Cell Transplantation," *Thrombosis and Haemostasis*, Jun. 2004; 91(6):1202-12.
Yang, H. et al., "Region-Specific Differentiation of Neural Tube-Derived Neuronal Restricted Progenitor Cells After Heterotopic Transplantation," *PNAS*, 2000; 97(24):13366-13371.
Ye Q. et al., "Recovery of Placental-Derived Adherent Cells With Mesenchymal Stem Cell Characteristics", *Blood*, 2001; 98(11 Part 2):147B (Abstract No. 4260).
Yeh, M.K., et al., "The preparation of sustained release erythropoietin microparticle," Journal of Microencapsulation, 2007 24(1):82-93.
Yip, H.K. and So, K.F., "Axonal Regeneration of Retinal Ganglion Cells: Effect of Trophic Factors," *Prog. Retin Eye Res.*, 2000; 19(5):559-575.
Yokoo, T. et al., "Stem Cell Gene Therapy for Chronic Renal Failure," *Curr Gene Ther.*, 2003; 3:387-94.
Zangani, D. et al., "Multiple Differentiation Pathways of Rat Mammary Stromal Cells In Vitro: Acquisition of a Fibroblast, Adipocyte or Endothelial Phenotype Is Dependent on Hormonal and Extracellular Matrix Stimulation," *Differentiation*, 1999; 64(2):91-101.
Zhang, L. et al., "A Test for Detecting Long-Term Sensorimotor Dysfunction in the Mouse after Focal Cerebral Ischemia," *J. Neurosci. Methods*, 2002; 117(2):207-214.
Zhang, S. et al., "In Vitro Differentiation of Transplantable Neural Precursors From Human Embryonic Stem Cells," *Nature Biotechnology*, 2001; 19:1129-33.
Zhang, X. et al., "Efficient Adeno-Associated Virus-Mediated Gene Expression in Human Placenta-Derived Mesenchymal Cells," *Microbiol. Immunol.*, 2003; 47(1):109-16.
Zhang, Y. et al., "Comparison of Mesenchymal Stem Cells from Human Placenta and Bone Marrow," *Chinese Medical Journal*, 2004; 117(6):882-87.
Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-92.

(56) References Cited

OTHER PUBLICATIONS

Zimmerman, S. et al., "Lack of Telomerase Activity in Human Mesenchymal Stem Cells," *Leukemia*, 2003; 17:1146-49.

Zuloff-Shani, A. et al., "Macrophage Suspensions Prepared From a Blood Unit for Treatment of Refractory Human Ulcers," *Transfus. Apheresis Sci.*, 2004; 30(2):163-67.

In the U.S. Patent and Trademark Office, Non-Final Office Action in re: U.S. Appl. No. 11/939,360 dated Oct. 7, 2010, 4 pages.

In the U.S Patent and Trademark Office, Final Office Action in re: U.S. Appl. No. 11/939,360 dated Mar. 15, 2011, 6 pages.

Wang, Y. et al., "Enhanced Recovery of Hematopoietic Progenitor and Stem Cells from Cultivated, Postpartum Human Placenta," *Blood*, 2001; 98(11): 183a (Abstract 769).

* cited by examiner

IN VITRO EXPANSION OF POSTPARTUM-DERIVED CELLS IN ROLLER BOTTLES

CROSS-REFERENCE TO RELATED APPLICATIONS

This application claims benefit to U.S. Provisional Patent Application No. 60/751,550, filed Dec. 19, 2005, the contents of which are incorporated by reference herein, in their entirety.

FIELD OF THE INVENTION

This relates generally to the growth and expansion of mammalian cells. In particular, this relates to methods for the in vitro growth and expansion of postpartum-derived cells in containers such as roller bottles.

BACKGROUND OF THE INVENTION

Commercial cell therapy products are preferably produced in aseptic systems that are closed. However, the growth of many cell lines used for commercial cell therapy products is anchorage-dependent. While stirred tank reactors, shaker flasks, spinner flasks, uplift reactors, and the like, are all useful for cells that grow in suspension (e.g. hybridomas for monoclonal antibody production, many cells used for recombinant DNA technology, and most insect cell cultures), the options for growing and expanding anchorage-dependent or anchorage-preferred cells are more limited.

Included among the anchorage-dependent cells are many normal diploid cell strains, as well as most primary cell lines. Options for large-scale production of such cells include roller bottles, fiber beds and hollow fiber systems, multi-plate or stacked-plate culture systems, cell cubes, and microcarriers, each of which has advantages and disadvantages.

Roller bottle-based methods of cell culture are probably the most commonly used method for growing anchorage-dependent and anchorage-preferred cells. Roller bottles are essentially cylindrical vessels, of glass or plastic, which are at least partially filled with a growth medium. Most modern roller bottles are made of a disposable plastic material. The bottles are placed on an apparatus that turns, causing the bottles to continuously "roll" or revolve at a typically constant speed of between about 5 and 250 revolutions per hour. The rolling motion allows the cells, which attach to the inside surfaces of the bottle, to bathe in the medium while having ample exchange of gases with the atmosphere in the bottles.

Roller bottles are available in various sizes, each size providing a fixed amount of surface area and volume. Many bottles are available in the 1-2 liter volume range. Two common sized commercial roller bottles provide 850 $cm^2$ and 1050 $cm^2$, respectively. For some applications, large size can be a limitation because roller bottles that are too large are difficult to handle where microbiological safety is critical. More recently roller bottles with expanded inner surfaces have become commercially available to help address the issue. Handling of roller bottle cultures, such as manipulations for subculture should be minimized where possible.

Roller bottle-based culture systems provide many advantages including relatively low cost for equipment and set-up, relative ease of set-up, and ability to scale up or down according to needs. The bottles, which are typically clear, allow for visual and microscopic inspection of the cells and the growth. Contaminated samples are easy to spot and can be discarded. The potential drawbacks include the relatively high level of skill required for seeding, transfers, harvest of cells or biologics produced, and other ongoing manipulation of the cells. The costs associated with ongoing operations may be high because of the skill level required. The risk of contamination is relatively high because of the amount of manipulation required. Notwithstanding the potential drawbacks, roller bottles are used still, even for the commercial production of some biologics.

Among the factors which should be considered in using roller bottles for cell culture are the attachment efficiency, as well as time to reach confluence, the growth parameters of attached cells including maximum attainable density per unit surface area, detachment techniques, which are required, and the efficiency of the detachment, scalability of the culture conditions, as well as homogeneity of the culture under scaled-up conditions, and the ability to successfully scale-up detachment procedures. Some of these considerations can be influenced by the inoculation parameters (such as rotational speed, media volume), culture conditions such as the rotational speed of the bottles, as well as the seeding density of the initial culture, the volume of medium used relative to the surface area and/or shape of the bottle, and the length of time the culture is incubated.

It is also important, particularly in cell therapeutic applications, that the characteristics of the cells grown under scaled-up roller bottle conditions be those of the desired cell type in terms of surface markers, gene expression, viability (over 70 to 80%), and the like.

There is a need to attempt to optimize the controllable culture parameters to improve roller bottle culture systems in terms of simultaneously maximizing the growth rate, the number of population doublings achieved, and the total cells available for harvest.

SUMMARY OF THE INVENTION

In one of its several aspects, the invention provides methods of maximizing the growth parameters of postpartum cells in roller bottle culture systems. In accordance with the invention, provided are methods of maximizing the number doublings of a culture of postpartum cells in a roller bottle culture system. The methods comprise using a rotational speed of at least about 0.85 rpm, using a media volume of at least about 100 ml in an 850 square centimeter culture bottle; using a seeding density of less than about 2500 cells per square centimeter; and incubating for at least about 5.5 days.

Also in accordance with the present invention are methods of maximizing the rate of doubling of a culture of postpartum cells in a roller bottle culture system. The methods for maximizing the rate of doubling preferably comprise using a rotational speed of at least about 0.85 rpm, using about 300 ml of growth medium in an 850 square centimeter culture bottle; using a seeding density of less than about 2500 cells per square centimeter; and incubating for less than about 6 days.

In another of its aspects, the invention provides methods of maximizing the density of cells at harvest for postpartum cells in a roller bottle culture system. These methods comprise using a rotational speed of about 0.5-1 rpm, using about 300 ml of growth medium in an 850 square centimeter culture bottle; using a seeding density of about 10,000 cells per square centimeter; and incubating for between about 5.5 to 6.7 days.

Also provided in accordance with one aspect of the invention are methods of simultaneously maximizing doubling rate, harvest density, and the total number of population doublings for postpartum cells in a roller bottle culture system.

These methods are also sometimes referred to herein as optimizing the roller bottle culture system for the foregoing parameters. The methods preferably comprise using a rotational speed of about 0.65-0.9 rpm, using at least about 300 ml of growth medium in an 850 square centimeter culture bottle; using a seeding density of less than about 2,500 cells per square centimeter; and incubating for between about 5.5 to 6.5 days.

The foregoing methods are particularly useful where the postpartum cells are umbilicus-derived cells, and presently preferred postpartum cells are those which are substantially similar, or even identical to ATCC NOS PTA-6067 and PTA-6068.

These and other aspects of the invention will be described with reference to the examples, figures, and detailed description of the various aspects of the invention which follow.

DETAILED DESCRIPTION OF ILLUSTRATIVE EMBODIMENTS

Figure 1:
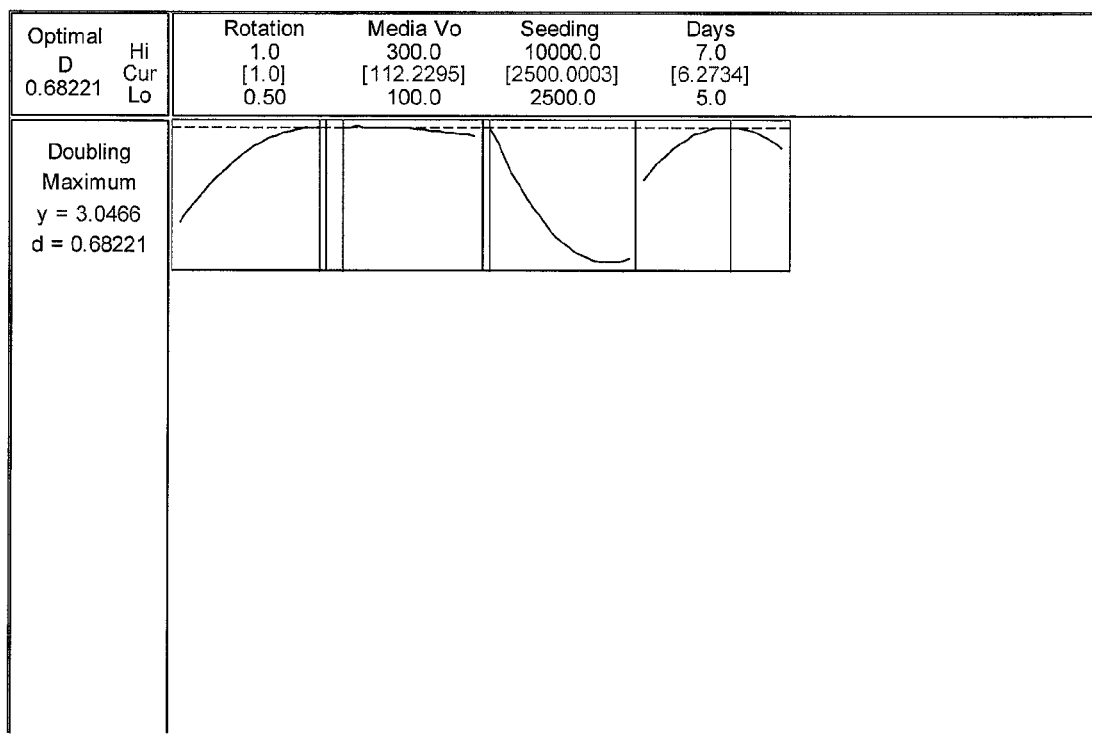
FIG. 1: Calculated optimal rotational speed (1.0 rpm), media volume (112 ml), seeding density (2,500 cells/cm sq.), and days in culture (6.27 days) to achieve the maximal population doublings (3.04). The black line on each graph represents the plotted values of the factor levels (low to high along the x-axis) vs. population doublings (minimal to maximal along the y-axis). The blue line represents the single maximum y-axis value for all four graphs. The red line represents the point on the x-axis that the plotted value of the factors levels vs. population doublings value (black line) intersects the single maximum y-axis value (blue line) thus defining the optimal factor level.

In several of its numerous aspects the invention provides separate methods of maximizing the amount of anchorage-dependent cells available for harvest from a population of cells grown in a roller bottle culture system, the growth rate of such a culture, or the total number of doublings of such a culture. The invention also provides methods for simultaneously maximizing all three of the foregoing parameters. Cells and populations of cells produced by the foregoing methods are also provided herein Roller bottle culture systems are known in the art of cell culture. As used herein, roller bottle culture systems comprise at least a cell line of interest, growth medium, roller bottles, an apparatus for rotating the bottles, and means for harvesting the cells. The growth medium preferably comprises a basal medium, for example, Dulbecco's Modified Eagle's Medium (DMEM), Advanced DMEM, Ham's F12, or combinations thereof, for example 1:1 DMEM:F 12. The medium can be supplemented with serum, for example in some embodiments the medium is supplemented with fetal bovine serum (FBS) or new born calf serum (NCS). The serum content can range in concentration from 0 (a serum-free media) to 20% of the total volume of the medium. Growth factors, for example, platelet derived growth factor BB (PDGF-BB), basic fibroblast growth factor (bFGF), and others, or combinations of such may be used to supplement the growth medium. Either serum-containing or serum-free media can be with or without growth factor supplementation.

Roller bottle culture systems typically further comprise means for controlling the temperature during the incubation, as well as means for aseptically handling the cultures, for example during initial seeding of the bottles with cells, or during subsequent transfers. Harvesting of the cells may be achieved through enzymatic treatment such as with trypsin, trypsin-EDTA, dispase, and collagenase, or other enzymes or combinations of enzymes with or without other components. Other commercial products such as but not limited to TrypLE™ Express (Gibco, Inc.) can be utilized. The cells also can be harvested by manual operations including, for example, batch centrifugation, or harvesting can be automated.

Presently the methods of maximizing the amount of cells available for harvest preferably are applied to postpartum-derived cells, particularly cells derived from the placenta or umbilicus. Cells of the type preferred here are described in U.S. patent application Ser. No. 10/877,446 (placenta-derived cells) and Ser. No. 10/877,012 (umbilicus-derived cells), each filed Jun. 25, 2004. The entireties of these applications are incorporated by reference herein. Also preferred are cells of the types available from the American Type Culture Collection as ATCC Accession Nos. PTA-6067; PTA-6068; PTA-6074; PTA-6075; or PTA-6079, the characterization and description of each of which is also incorporated by reference herein. Particularly preferred for the present methods directed to maximized or optimized methods for culturing umbilical-derived cells, for example, are ATCC Accession Nos. PTA-6067 and PTA-6068.

In one of its several aspects the invention provides methods of maximizing the number of population doublings achievable for a population of cells grown in a roller bottle culture system. Preferably the cells are postpartum-derived cells, and even more preferably the cells are umbilicus-derived cells. In a presently preferred embodiment the cells are ATCC Accession No: PTA-6067 or PTA-6068.

The independent variables which have been used to maximize the number of population doublings achievable in a roller bottle culture are rotational speed, seeding density of the cells into the bottles, time of incubation, and volume of medium placed in the bottle. Herein and throughout in the embodiments exemplified these independent variables have been tested, for reasons of practicality, within certain ranges. The skilled artisan will appreciate that other values outside of the tested ranges could be routinely tested using the same methodology, and these values may prove to offer incremental gains in the number of population doublings. Maximal response of the dependent variable, here the number of population doublings achieved is measured as a function of these parameters and embodiments not specifically exemplified herein are contemplated as part of this disclosure.

To help maximize the dependent variable as a function of the four independent variables, regression analysis was used. In particular, response surface methodology (RSM) is presently a preferred approach to optimize culture growth parameters. Applications of RSM to optimization techniques are known in the art. RSM allows optimization of multiple independent parameters to achieve a desired or optimal response. Parameter sets that provide maximal and minimal responses can be accurately determined using RSM.

As can be seen from the data exemplified herein and below, the independent variables tested can reproducibly affect the maximal number of population doublings. Thus, the statistical analysis of the data allows the skilled artisan to determine the optimal value for each of the four independent variables to maximize the number of doublings.

In a preferred embodiment, therefore, the bottles are filled about 100-300 ml of growth medium, in other embodiments about 100-200 ml are used, as can be seen from FIG. 1. In one embodiment about 100-120 ml, or even 105-115 ml are placed in the bottles. In other embodiments, the bottles are filled with about 112 ml of growth medium to achieve maximal population doublings. The bottles are seeded with about 2500 to about 10,000 cells per square centimeter. In a preferred embodiment, the lower end of that range is used, for example seeding is with less than about 3000 cells per square centimeter. As can be seen from FIG. 1, still more preferred are embodiments where the seeding is at an even lower end of the tested range—the seeding is done with about 2500 cells per square centimeter. The seeding bottles are rotated during attachment and growth. The rotational speed is set at between about 0.5 to 1 rpm. Preferably, the rotation is between about 0.75 and 1 rpm. More preferably, the bottles are rotated at about 0.8 to 1 rpm. Rotation near or about 1 rpm is preferred as can be seen in FIG. 1.

The filled and seeded roller bottles are rotated and incubated for about 5 to 7 days to achieve maximal doublings. Presently, an incubation time of about 5.5 to about 6.5 days is preferred. As FIG. 1 reflects, incubation for about 6.2 to 6.3 days is also preferred.

It can also be seen from FIG. 1 that the independent variable can be selected as a set of parameters to maximize the number of population doublings. A roller bottle culture system that comprises a fill volume of about 112 ml of growth medium, and a seeding density of about 2500 cells per square centimeter, which is rotated at a speed of about 1 rpm for an incubation of about 6.2 days will provide the maximal population doublings achievable in such a system.

It may be noted that the roller bottles preferred for use are typically coated with an agent that aids in the attachment of the cells to the inner surface of the roller bottles, such as gelatin, extracellular matrix molecules (such as gelatin, laminin, vitronectin, fibronectin, collagen types I, IV, and VI), or the like. While for many of the embodiments exemplified, a gelatin coating was used, other coatings are deemed suitable and the skilled artisan will appreciate that commercially-available coated bottles are completely compatible with the methods taught herein. One example of such commercially available coated bottles are those coated with CellBIND® (available from Corning® as catalog number 3907). The use of CellBIND® bottles and a comparison with gelatin-coated bottles is exemplified in Example 4 below. It is envisioned that various coating agents will be found acceptable for attachment and growth of cells in accordance with the methods provided herein.

In another of its aspects, the invention provides methods of minimizing the number of hours/population doubling (see FIG. 2), or alternatively expressed, maximizing the population doubling rate for a population of cells grown in a roller bottle culture system. As used herein the population doubling rate is the number of population doublings per unit time, and is a reciprocal of the hours per population doubling. Achieving maximal population doubling rate reduces the amount of time required to produce a needed number of cell for therapeutic applications and increases the total throughput of a culture system of limited capacity. As above and throughout this disclosure, preferably the cells are postpartum-derived cells, and even more preferably the cells are umbilicus-derived cells. In a presently preferred embodiment the cells are ATCC Accession No: PTA-6067 or PTA-6068.

The independent variables which have been used to maximize the number of population doublings achievable in a roller bottle culture are the same as for achieving the maximal number of population doublings: rotational speed, seeding density of the cells into the bottles, time of incubation, and volume of medium placed in the bottle. Maximal response of the dependent variable, here the population doubling rate, is measured and computed as a function of these parameters.

Regression analysis, and particularly RSM was again employed to help maximize the dependent variable as a function of the four independent variables.

Figure 2:
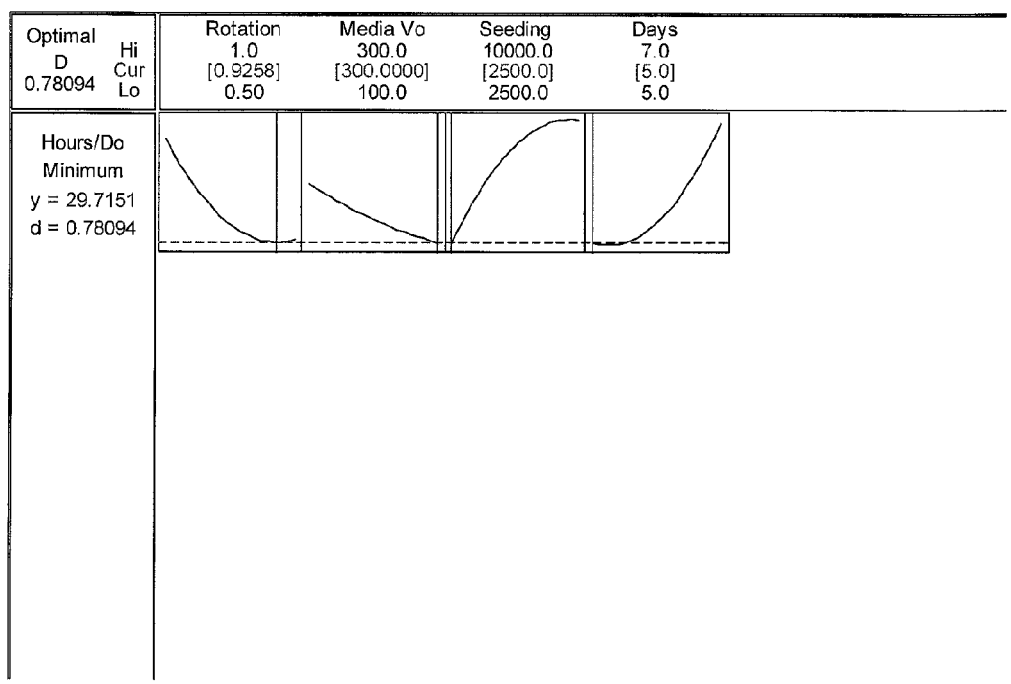
FIG. 2: Calculated optimal rotational speed (0.92 rpm), media volume (300 ml), seeding density (2,500 cells/cm sq.), and days in culture (5 days) to achieve the minimal hours per population doubling (29.71). The black line on each graph represents the plotted values of the factor levels (low to high along the x-axis) vs. hours per population doublings (minimal to maximal along the y-axis). The blue line represents the single maximum y-axis value for all four graphs. The red line represents the point on the x-axis that the plotted value of the factors levels vs. hours per population doublings value (black line) intersects the single minimum y-axis value (blue line) thus defining the optimal factor level.

Thus, in a presently preferred embodiment, roller bottles are filled about 100-300 ml of growth medium, preferably about 300 ml are used, as can be seen from FIG. 2. The bottles are seeded with about 2500 to about 10,000 cells per square centimeter. In a presently preferred embodiment, the lower end of that range is used, for example seeding is with less than about 3000 cells per square centimeter. Still more preferred are embodiments where the seeding is at about 2500 cells per square centimeter. The seeded bottles are rotated during attachment and growth. The rotational speed is set at between about 0.5 to 1 rpm, as can be seen from FIG. 2. Preferably, the rotation is between about 0.75 and 1 rpm. More preferably, the bottles are rotated at about 0.8 to 1 rpm. Rotation near or about 0.9-1.0 rpm is presently preferred, as shown in the figure.

To maximize the population doubling rate, the filled and seeded roller bottles are rotated and incubated for about 5 to 7 days, with an incubation time of about 5 to about 6 days preferred. FIG. 2 shows that incubation for about 5 days is also preferred.

The independent variables can be selected as a set of parameters to maximize the population doubling rate, based on the results shown in FIG. 2. A roller bottle culture system that comprises a fill volume of about 300 ml of growth medium, and a seeding density of about 2500 cells per square centimeter, which is rotated at a speed of about 0.9 rpm for an incubation of about 5 days will provide the maximal population doubling rate achievable in such a system.

In another of its several aspects the invention provides methods of maximizing the density of anchorage-dependent cells available for harvest from a population of cells grown in a roller bottle culture system. As above, preferably the cells are postpartum-derived cells, and even more preferably the cells are umbilicus-derived cells. In a presently preferred embodiment the cells are ATCC Accession No: PTA-6067 or PTA-6068.

In another of its aspect, the invention provides methods of maximizing the density of the cell population for harvest for a population of cells grown in a roller bottle culture system. Harvest density is expressed as the number of cells per square centimeter (of internal surface area in a roller bottle).

The independent variables which have been used to maximize the harvest density in a roller bottle culture are the same as those for maximizing the other responses discussed herein, i.e rotational speed, seeding density of the cells into the bottles, time of incubation, and volume of medium placed in the bottle. Maximal response of the harvest density is measured and computed as a function of these parameters.

Regression analysis, and particularly RSM was employed here as above to help maximize the dependent variable as a function of the four independent variables.

Figure 3:
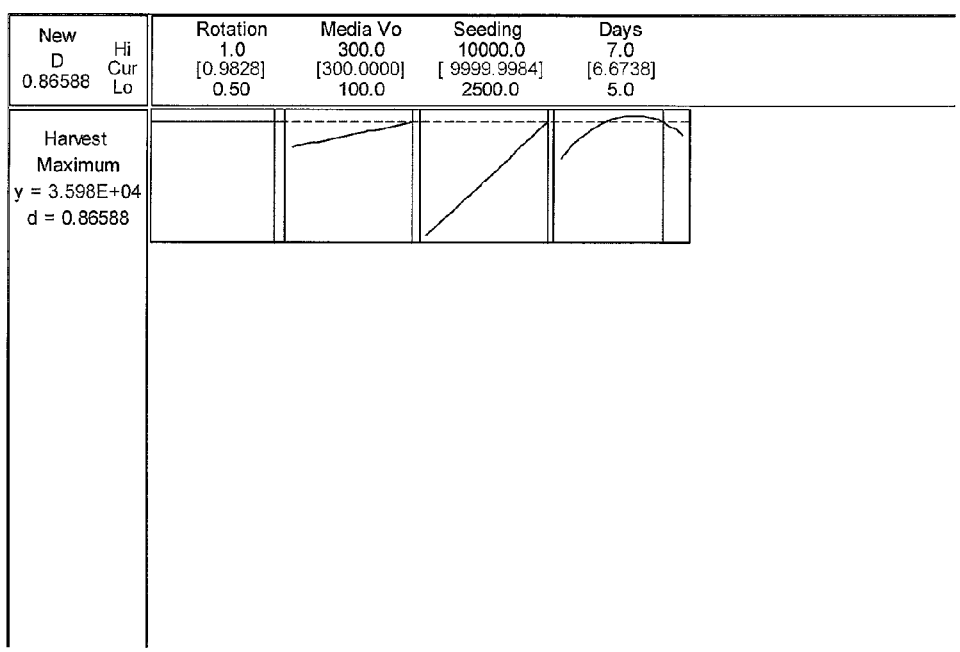
FIG. 3: Calculated optimal rotational speed (0.98 rpm), media volume (300 ml), seeding density (10,000 cells/cm sq.), and days in culture (6.67 days) to achieve the maximal harvest density (cell/cm sq.) (3.59E+04). The black line on each graph represents the plotted values of the factor levels (low to high along the x-axis) vs. maximal harvest density (minimal to maximal along the y-axis). The blue line represents the single maximum y-axis value for all four graphs. The red line represents the point on the x-axis that the plotted value of the factors levels vs. maximal harvest density (black line) intersects the single maximum y-axis value (blue line) thus defining the optimal factor level.

Maximal response of the dependent variable, here the density of cells available for harvesting is calculated as a function of these parameters. In a presently preferred embodiment, roller bottles are filled about 100-300 ml of growth medium, preferably about 300 ml are used, as can be seen from FIG. 3. The bottles are seeded with about 2500 to about 10,000 cells per square centimeter, preferably the seeding density is selected from the lower end of that range, such as a value less than about 3000 cells per square centimeter. More preferred are those embodiments wherein seeding density is at about 2500 cells per square centimeter. The seeded bottles are rotated throughout attachment and growth at a speed between about 0.5 to 1 rpm, as shown in FIG. 3. In preferred embodiments, rotation is between about 0.75 and 1 rpm. More preferably, the bottles are rotated at about 0.8 to 1 rpm. Rotation near or about 0.9-1.0 rpm is presently preferred, for example 0.98 rpm, as shown in the figure.

To maximize the harvest density of the cultured cells, the filled and seeded roller bottles are rotated and incubated for about 5 to 7 days, with an incubation time of about 6 to about 7 days preferred. FIG. 3 shows that incubation for about 5.8 to less than about 6 days or for about 6.5 to about 6.7 days is also preferred.

In another aspect, the invention provides methods of simultaneously minimizing the number of hours/population doubling, while maximizing the number of population doublings and the harvest density (in cells per square centimeter) for a population of cells grown in a roller bottle culture system. Such optimization of the culture conditions makes the roller bottle culture system more useful for generating the number of cells required for a therapeutic application and increases the total throughput of a culture system of limited capacity. As above, preferably the cells are postpartum-derived cells, and even more preferably the cells are umbilicus-derived cells. In a presently preferred embodiment the cells are ATCC Accession No: PTA-6067 or PTA-6068.

The independent variables which have been adjusted to help simultaneously maximize the number of population doublings achievable, the rate of population doublings and the final harvest density of the cells in a roller bottle culture are the same as detailed above for maximizing the individual aspects: i.e. rotational speed, seeding density of the cells into the bottles, time of incubation, and volume of medium placed in the bottle. Maximal response of the dependent variables is measured and calculated as a function of these independent parameters.

As above, regression analysis, and particularly RSM was utilized to help simultaneously maximize the three dependent variables as a function of the four independent variables.

Figure 4:
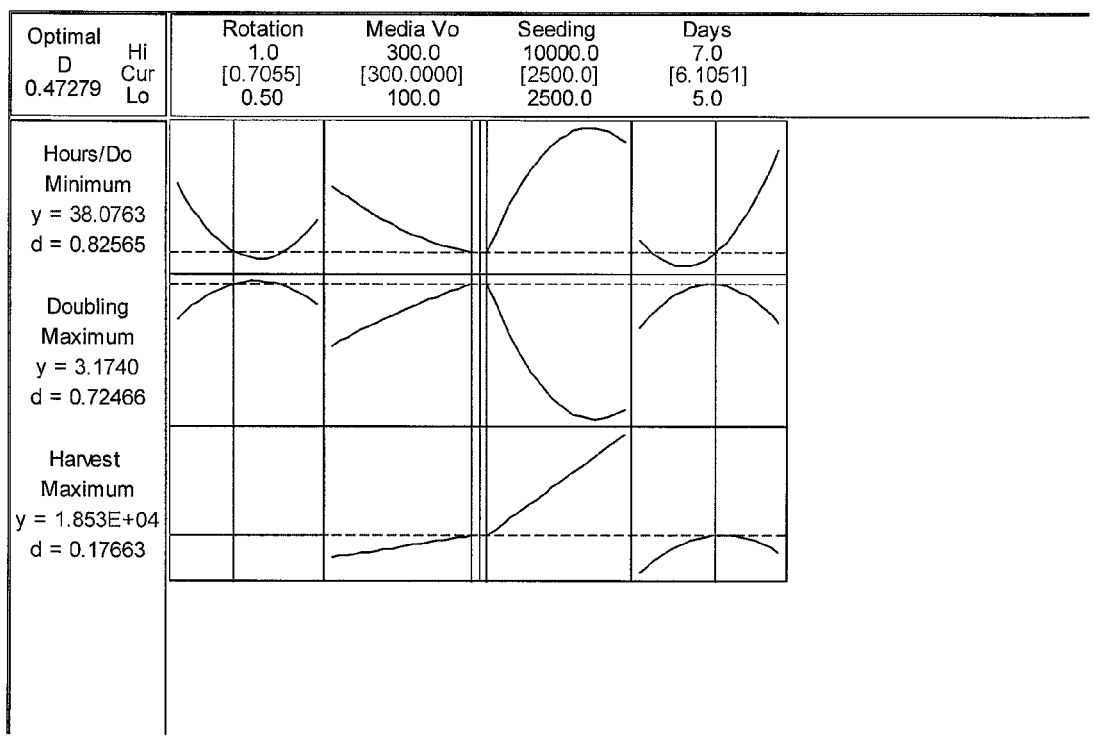
FIG. 4: Calculated optimal rotational speed (0.705 rpm), media volume (300 ml), seeding density (2,500 cells/cm sq.), and days in culture (6.1 days) to achieve the minimum hours/population doubling (38.07 hours), maximum population doublings (3.17), and maximum harvest density (cell/cm sq.) (1.8E+04). The black lines on each graph represent the plotted values of the factor levels (low to high along the x-axis) vs. response values (minimal to maximal along the y-axis). The blue line represents the single maximum, or minimal, y-axis value for all four graphs. The red line represents the point on the x-axis that the plotted value of the factors levels vs. response value (black line) intersects the single maximum y-axis value for population doublings and harvest density and the minimum y-axis value for hours per population doubling (blue line) thus defining the optimal factor levels.
Figure 5:
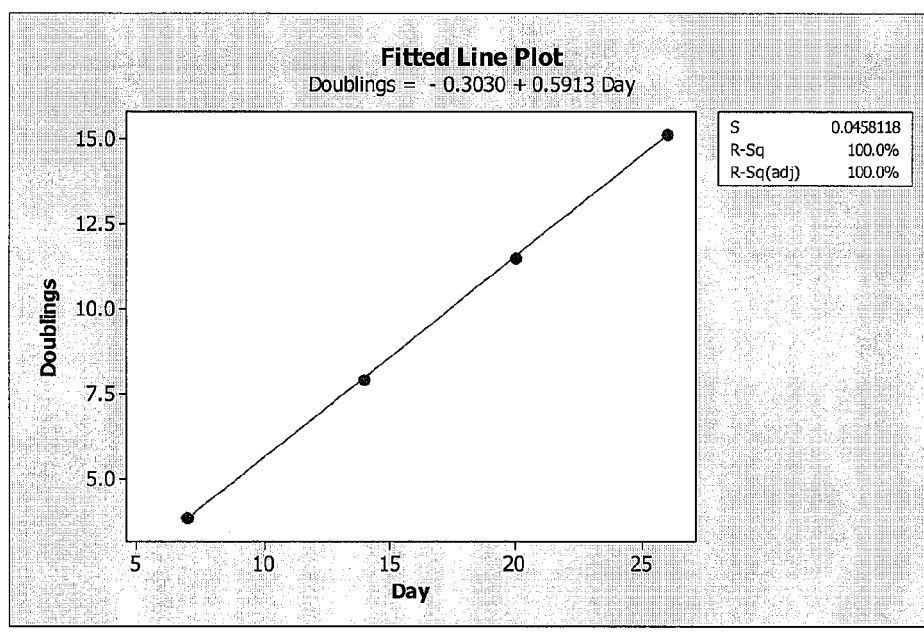
FIG. 5: Population Doublings vs. Days in Culture of umbilical cell line 050604B expanded from passage six to passage nine under optimized roller bottle culture conditions

Thus, in preferred embodiments, roller bottles are filled about 100-300 ml of growth medium, preferably about 300 ml are used, as can be seen with reference to FIG. 4. The bottles are seeded with about 2500 to about 10,000 cells per square centimeter. In a presently preferred embodiment, the lower end of that range is used, for example seeding is with less than about 3000 cells per square centimeter. Still more preferred are embodiments where the seeding is at about 2500 cells per square centimeter. Even lower seeding density is used is other embodiments. The seeded bottles are rotated during attachment and growth at speeds between about 0.5 to 1 rpm. With further reference to FIG. 4, in can be seen that preferably, the rotation is between about 0.6 and 0.9 rpm. More preferably, the bottles are rotated at about 0.65 to 0.93 rpm. Also preferred are culture systems wherein the rotation is near or about 0.85-0.9 rpm as can be seen in the figure.

To further optimize the roller bottle culture, the filled and seeded roller bottles are rotated and incubated for about 5 to 7 days, with an incubation time of about 5.5 to about 6.5 days preferred. FIG. 4 shows that incubation for about 6 days is also preferred, such as 5.9, 6.0, 6.1 or 6.2 days.

In a presently preferred culture system, the independent variables can be selected as a set of parameters to maximize the population doubling rate, based on the results shown in FIG. 4. A roller bottle culture system that comprises a fill volume of about 300 ml of growth medium, and a seeding density of about 2500 cells per square centimeter, which is rotated at a speed of about 0.7 rpm for an incubation of about 6.1 days will provide the optimal population doubling rate, total number of doublings and harvest density for the cells achievable in such a system.

In another aspect, the invention provides postpartum cells, preferably umibilicus-derived cells, that are produced are produced by any of the methods of the invention, for example the maximized methods or optimized. In various embodiments, the cells are produced in populations for use as cell therapeutics, or to provide useful cellular product or by-products, such as useful cellular factors, or proteins.

Also provided are cell therapeutic compositions comprising cells cultured by the methods provided herein.

In another aspect of the invention, the cells that are cultured according to the methods provided are characterized as having substantially the same cell surface marker profile or gene expression profile as the starting cells. For many applications of cell-based therapies it is important that the cellular characteristics do not change when scaling up the culture conditions to increase quantities. For example, the morphology, cell surface markers, and expression of hallmark genes that help distinguish or denote the therapeutic cell should remain substantially unchanged if not identical. The cells provided in accordance with the invention and the methods taught therein are substantially unchanged, or preferably identical in such characteristics as the same cells grown under laboratory conditions ad scale. The preferred umbilicus-derived cells retain substantially the same the cell surface marker profile of the cells from which they are grown. Preferably, the cells produced according to the methods provided herein express more than one of surface markers for CD10, CD13, CD44, CD73, CD90, PDGFr-alpha, and HLA-ABC. More preferably they express all of these markers. The cells also preferably do not express more than one of the cell surface markers for CD31, CD34, CD45, CD117, CD 141, and HLA-DRDPDQ. More preferably the cells do not express any of the foregoing. In a highly preferred embodiment, the cells express an identical cell surface marker profile with respect to each of CD10, CD13, CD44, CD73, CD90, PDGFr-alpha, HLA-ABC, CD31, CD34, CD45, CD117, CD141, and HLA-DRDPDQ. Moreover, preferred cells are positive for expression of CD 10, CD 13, CD44, CD73, CD90, PDGFr-alpha, and HLA-ABC, but negative for expression of CD31, CD34, CD45, CD117, CD141, and HLA-DRDPDQ. The skilled artisan will appreciate that are several ways to assess the cell surface marker profile of a cell line. As used herein, if a cell surface marker protein can be detected through use of a fluorescently-labeled antibody the cell is deemed positive and if the cell surface marker cannot be detected via fluorescent antibody, the cell is deemed negative for that marker. Table 6 provides a summary of the preferred cell surface markers for the umbilicus-derived cells of the invention.

In similar fashion, the cells produced in accordance with the methods of the invention preferably retain substantially the same, or even identical gene expression profile, particularly for genes whose expression help to characterize the cell, or serve as hallmarks indicative of that cell line. The umbilicus-derived cells of the invention are noted for the expression genes for reticulon, LDL-R, IL-8, and GAPDH. The cells provided are substantially similar, or even identical in various embodiments with respect to their expression of these genes.

These and other aspects of the invention are further described with reference to the figures and examples provided below. The skilled artisan will appreciate that the examples are provided to exemplify only certain aspects of the invention and not to limit the invention.

Example 1

Optimization Experiments for Determining Culture Condition Parameters

Cells: The cells used were from umbilicus-derived cell line ATCC Accession Nos. PTA-6067 and/or PTA-6068.

Media: The growth medium used during the optimization experiments was Dulbecco's Modified Eagle Medium (DMEM) with low glucose, 15% Fetal Bovine Serum, 1% Penicillin-Streptomycin, and 1 ppm 2-Mercaptoethanol.

Bottles: 850 cm sq bottles were used (e.g. Corning® catalog number 430851).

Gelatin Coating: Twenty (20) ml of 2% gelatin solution were added to each 850 cm sq bottle. The bottles were placed on the roller system for 20 minutes at 1 rpm. The excess gelatin solution was removed by aspiration and the bottles washed with 20 ml Phosphate Buffered Saline (PBS).

Cell Seeding: P13 Umbilical 022803 cells from frozen stock cells were thawed from a cryogenic vial and washed to remove dimethyl sulfoxide (DMSO). Cells were seeded into single 850 cm sq roller bottle pre-filled with 300 ml media and pre-gassed for 1 minute with compressed air containing 5% $CO_2$, 95% atmospheric gas.

Incubation: Cells were cultured in a temperature-controlled room set at 37° C.

Harvesting: Media was removed from each roller bottle by aspiration and adherent cells were washed with 50 ml PBS. PBS was removed by aspiration and 10 ml of trypsin-ethylenediaminetetraacetic acid (EDTA) was added to aid in the release of the cells from the roller bottle surface. Bottles were returned to the roller system and incubated for 5 minutes at 0.75 RPM. After incubation, 40 ml of media was added to each bottle. The media with cells was then transferred to a 50 ml conical tube and centrifuged for 5 minutes at 300×g. After centrifugation, the media was removed by aspiration and each cell pellet was re-suspended in 10 ml of media. Cells were counted using a Beckman Coulter Cedex® instrument.

Statistical Model: A Box-Behnken Response Surface model was used.

Experimental design and optimization were calculated using a Minitab 14.0. the parameters tested are shown in Table 1

TABLE 1

Factors tested and the range of values tested.

| Factor | Low | High |
| --- | --- | --- |
| Rotational Speed (rpm) | 0.5 | 1 |
| Media Volume (ml) | 100 | 300 |
| Seeding Density (cells/cm sq) | 2,500 | 10,000 |
| Days | 5 | 7 |

Experimental Design: Experiments as provided in Table 1 were set up in accordance with the above procedures.

TABLE 2

Box-Behnken Response Surface Experimental Design to evaluate the factors and factor interactions that significantly effect cell yield as calculated by Minitab 14.0 statistical software. The highest and lowest factor levels for rotational speed (low 0.5 rpm, high 1.0 rpm), media volume (low 100 ml, high 500 ml), seeding density (low 2,500 cell/cm sq., high 10,000 cells/cm sq.) and days in culture (low 5 days, high 7 days) are user-defined and the mid point is calculated.

| Run Order | Rotational Speed (rpm) | Media Volume (ml) | Seeding Density (cells/cm sq) | Days |
| --- | --- | --- | --- | --- |
| 1 | 0.5 | 200 | 6,250 | 5 |
| 2 | 1 | 200 | 6,250 | 7 |
| 3 | 0.75 | 300 | 6,250 | 7 |
| 4 | 1 | 200 | 10,000 | 6 |
| 5 | 0.75 | 200 | 6,250 | 6 |
| 6 | 0.75 | 200 | 2,500 | 5 |
| 7 | 1 | 300 | 6,250 | 6 |
| 8 | 0.5 | 200 | 6,250 | 7 |
| 9 | 0.5 | 300 | 6,250 | 6 |
| 10 | 1 | 100 | 6,250 | 6 |
| 11 | 0.5 | 200 | 10,000 | 6 |
| 12 | 0.75 | 300 | 6,250 | 5 |
| 13 | 0.75 | 200 | 10,000 | 5 |
| 14 | 0.75 | 200 | 2,500 | 7 |
| 15 | 0.5 | 100 | 6,250 | 6 |
| 16 | 1 | 200 | 2,500 | 6 |
| 17 | 0.75 | 100 | 2,500 | 6 |
| 18 | 0.75 | 300 | 2,500 | 6 |
| 19 | 0.5 | 200 | 2,500 | 6 |
| 20 | 1 | 200 | 6,250 | 5 |
| 21 | 0.75 | 200 | 6,250 | 6 |
| 22 | 0.75 | 100 | 6,250 | 7 |
| 23 | 0.75 | 200 | 10,000 | 7 |
| 24 | 0.75 | 100 | 10,000 | 6 |
| 25 | 0.75 | 200 | 6,250 | 6 |
| 26 | 0.75 | 300 | 10,000 | 6 |
| 27 | 0.75 | 100 | 6,250 | 5 |

TABLE 3

Cells yield obtained from factor levels defined by Box-Behnken response surface experimental design. Harvest Density is expressed in cells/cm$^2$.

| Bottle | Seeded | Yield | Expansion | Doublings | Time (days) | Hours/ doubling | Harvest Density |
|---|---|---|---|---|---|---|---|
| 1 | 5.31E+06 | 9.80E+06 | 1.84 | 0.88 | 5 | 136 | 1.15E+04 |
| 2 | 5.31E+06 | 1.68E+07 | 3.16 | 1.66 | 7 | 101 | 1.98E+04 |
| 3 | 5.31E+06 | 1.50E+07 | 2.82 | 1.5 | 7 | 112 | 1.76E+04 |
| 4 | 8.50E+06 | 1.86E+07 | 2.19 | 1.13 | 6 | 127 | 2.19E+04 |
| 5 | 5.31E+06 | 2.10E+07 | 3.95 | 1.98 | 6 | 73 | 2.47E+04 |
| 6 | 2.13E+06 | 1.23E+07 | 5.79 | 2.53 | 5 | 47 | 1.45E+04 |
| 7 | 5.31E+06 | 2.17E+07 | 4.08 | 2.03 | 6 | 71 | 2.55E+04 |
| 8 | 5.31E+06 | 1.62E+07 | 3.04 | 1.6 | 7 | 105 | 1.90E+04 |
| 9 | 5.31E+06 | 2.78E+07 | 5.23 | 2.39 | 6 | 60 | 3.27E+04 |
| 10 | 5.31E+06 | 1.96E+07 | 3.69 | 1.88 | 6 | 76 | 2.31E+04 |
| 11 | 8.50E+06 | 2.94E+07 | 3.46 | 1.79 | 6 | 80 | 3.46E+04 |
| 12 | 5.31E+06 | 1.58E+07 | 2.97 | 1.57 | 5 | 76 | 1.86E+04 |
| 13 | 8.50E+06 | 3.03E+07 | 3.56 | 1.83 | 5 | 65 | 3.56E+04 |
| 14 | 2.13E+06 | 1.50E+07 | 7.06 | 2.82 | 7 | 60 | 1.76E+04 |
| 15 | 5.31E+06 | 1.31E+07 | 2.47 | 1.3 | 6 | 111 | 1.54E+04 |
| 16 | 2.13E+06 | 1.59E+07 | 7.48 | 2.9 | 6 | 50 | 1.87E+04 |
| 17 | 2.13E+06 | 1.47E+07 | 6.92 | 2.79 | 6 | 52 | 1.73E+04 |
| 18 | 2.13E+06 | 1.84E+07 | 8.66 | 3.11 | 6 | 46 | 2.16E+04 |
| 19 | 2.13E+06 | 1.22E+07 | 5.74 | 2.52 | 6 | 57 | 1.44E+04 |
| 20 | 5.31E+06 | 1.63E+07 | 3.07 | 1.62 | 5 | 74 | 1.92E+04 |
| 21 | 5.31E+06 | 2.21E+07 | 4.16 | 2.06 | 6 | 70 | 2.60E+04 |
| 22 | 5.31E+06 | 1.77E+07 | 3.33 | 1.74 | 7 | 97 | 2.08E+04 |
| 23 | 8.50E+06 | 3.48E+07 | 4.1 | 2.04 | 7 | 83 | 4.10E+04 |
| 24 | 8.50E+06 | 3.55E+07 | 4.18 | 2.06 | 6 | 70 | 4.18E+04 |
| 25 | 5.31E+06 | 2.23E+07 | 4.2 | 2.07 | 6 | 70 | 2.62E+04 |
| 26 | 8.50E+06 | 3.40E+07 | 4 | 2 | 6 | 72 | 4.00E+04 |
| 27 | 5.31E+06 | 1.14E+07 | 2.15 | 1.1 | 5 | 109 | 1.34E+04 |

TABLE 4

Response Surface Regression Analysis: Harvest Density (cells/cm$^2$) versus Rotational Speed, Media Volume, Seeding Density and Days in Culture.

Estimated Regression Coefficients for Harvest Density (coded units)

| Term | Coef | SE Coef | T | P |
|---|---|---|---|---|
| Constant | 25647.1 | 2841 | 9.028 | 0.000 |
| Rotational Speed (rpm) | 43.1 | 1420 | 0.030 | 0.976 |
| Media Volume (ml) | 2029.4 | 1420 | 1.429 | 0.179 |
| Seeding Density (cells/cm sq) | 9229.4 | 1420 | 6.498 | 0.000 |
| Days | 1921.6 | 1420 | 1.353 | 0.201 |
| Rotational Speed (rpm) * Rotational Speed (rpm) | −4010.8 | 2131 | −1.882 | 0.084 |
| Media Volume (ml) *Media Volume (ml) | 9.8 | 2131 | 0.005 | 0.996 |
| Seeding Density (cells/cm sq) * Seeding Density (cells/cm sq) | 3898.0 | 2131 | 1.830 | 0.092 |
| Days*Days | −4887.3 | 2131 | −2.294 | 0.041 |
| Rotational Speed (rpm) * Media Volume (ml) | −3705.9 | 2460 | −1.506 | 0.158 |
| Rotational Speed (rpm) * Seeding Density (cells/cm sq) | −4264.7 | 2460 | −1.733 | 0.109 |
| Rotational Speed (rpm) *Days | −1723.5 | 2460 | −0.701 | 0.497 |
| Media Volume (ml) * Seeding Density (cells/cm sq) | −1529.4 | 2460 | −0.622 | 0.546 |
| Media Volume (ml) *Days | −2088.2 | 2460 | −0.849 | 0.413 |
| Seeding Density (cells/cm sq) *Days | 541.2 | 2460 | 0.220 | 0.830 |

S = 4920 R-Sq = 85.3% R-Sq(adj) = 68.2%

Analysis of Variance for Harvest Density

| Source | DF | Seq SS | Adj SS | Adj MS | F | P |
|---|---|---|---|---|---|---|
| Regression | 14 | 1691605592 | 1691605592 | 120828971 | 4.99 | 0.004 |
| Linear | 4 | 1115938309 | 1115938309 | 278984577 | 11.52 | 0.000 |
| Square | 4 | 408129068 | 408129068 | 102032267 | 4.21 | 0.023 |
| Interaction | 6 | 167538215 | 167538215 | 27923036 | 1.15 | 0.391 |
| Residual Error | 12 | 290519868 | 290519868 | 24209989 | | |

TABLE 4-continued

Response Surface Regression Analysis: Harvest Density (cells/cm$^2$) versus Rotational Speed, Media Volume, Seeding Density and Days in Culture.

| | | | | | | |
|---|---|---|---|---|---|---|
| Lack-of-Fit | 10 | 289163467 | 289163467 | 28916347 | 42.64 | 0.023 |
| Pure Error | 2 | 1356401 | 1356401 | 678200 | | |
| Total | 26 | 1982125460 | | | | |

Unusual Observations for Harvest Density

| Obs | StdOrder | Harvest Density | Fit | SE Fit | Residual | St Resid |
|---|---|---|---|---|---|---|
| 4 | 12 | 21882.350 | 30542.156 | 3757.991 | −8659.806 | −2.73 R |

(R denotes an observation with a large standardized residual.)

Estimated Regression Coefficients for Harvest Density (uncoded units)

| Term | Coef |
|---|---|
| Constant | −3.05951E+05 |
| Rotational Speed (rpm) | 195874.5033 |
| Media Volume (ml) | 281.8629 |
| Seeding Density (cells/cm sq) | 2.3578 |
| Days | 69013.6992 |
| Rotational Speed (rpm) * Rotational Speed (rpm) | −64172.5667 |
| Media Volume (ml) *Media Volume (ml) | 0.0010 |
| Seeding Density (cells/cm sq) * Seeding Density (cells/cm sq) | 0.0003 |
| Days*Days | −4887.2529 |
| Rotational Speed (rpm) * Media Volume (ml) | −148.2353 |
| Rotational Speed (rpm) * Seeding Density (cells/cm sq) | −4.5490 |
| Rotational Speed (rpm) *Days | −6894.1100 |
| Media Volume (ml) * Seeding Density (cells/cm sq) | −0.0041 |
| Media Volume (ml) *Days | −20.8824 |
| Seeding Density (cells/cm sq) *Days | 0.1443 |

TABLE 5

Response Surface Regression Analysis: Hours/Doubling versus Rotational Speed, Media Volume, Seeding Density and Days in Culture.

Estimated Regression Coefficients for Hours/Doubling (coded units)

| Term | Coef | SE Coef | T | P |
|---|---|---|---|---|
| Constant | 70.740 | 10.095 | 7.008 | 0.000 |
| Rotational Speed (rpm) | −4.098 | 5.047 | −0.812 | 0.433 |
| Media Volume (ml) | −6.351 | 5.047 | −1.258 | 0.232 |
| Seeding Density (cells/cm sq) | 15.516 | 5.047 | 3.074 | 0.010 |
| Days | 4.068 | 5.047 | 0.806 | 0.436 |
| Rotational Speed (rpm) * Rotational Speed (rpm) | 14.990 | 7.571 | 1.980 | 0.071 |
| Media Volume (ml) *Media Volume (ml) | 2.919 | 7.571 | 0.386 | 0.707 |
| Seeding Density (cells/cm sq) * Seeding Density (cells/cm sq) | −14.948 | 7.571 | −1.974 | 0.072 |
| Days*Days | 17.023 | 7.571 | 2.248 | 0.044 |
| Rotational Speed (rpm) * Media Volume (ml) | 11.188 | 8.742 | 1.280 | 0.225 |
| Rotational Speed (rpm) * Seeding Density (cells/cm sq) | 13.635 | 8.742 | 1.560 | 0.145 |
| Rotational Speed (rpm) *Days | 14.528 | 8.742 | 1.662 | 0.122 |
| Media Volume (ml) * Seeding Density (cells/cm sq) | 1.885 | 8.742 | 0.216 | 0.833 |
| Media Volume (ml) *Days | 12.015 | 8.742 | 1.374 | 0.194 |
| Seeding Density (cells/cm sq) *Days | 1.222 | 8.742 | 0.140 | 0.891 |

S = 17.48 R-Sq = 76.4% R-Sq(adj) = 48.9%

Analysis of Variance for Hours/Doubling

| Source | DF | Seq SS | Adj SS | Adj MS | F | P |
|---|---|---|---|---|---|---|
| Regression | 14 | 11898.4 | 11898.42 | 849.89 | 2.78 | 0.042 |
| Linear | 4 | 3773.1 | 3773.06 | 943.27 | 3.09 | 0.058 |

TABLE 5-continued

Response Surface Regression Analysis: Hours/Doubling versus Rotational Speed, Media Volume, Seeding Density and Days in Culture.

|  |  |  |  |  |  |  |
| --- | --- | --- | --- | --- | --- | --- |
| Square | 4 | 5439.2 | 5439.24 | 1359.81 | 4.45 | 0.020 |
| Interaction | 6 | 2686.1 | 2686.12 | 447.69 | 1.46 | 0.270 |
| Residual Error | 12 | 3668.4 | 3668.38 | 305.70 |  |  |
| Lack-of-Fit | 10 | 3663.0 | 3662.98 | 366.30 | 135.71 | 0.007 |
| Pure Error | 2 | 5.4 | 5.40 | 2.70 |  |  |
| Total | 26 | 15566.8 |  |  |  |  |

Unusual Observations for Hours/Doubling

| Obs | StdOrder | Hours/Doubling | Fit | SE Fit | Residual | St Resid |
| --- | --- | --- | --- | --- | --- | --- |
| 4 | 12 | 127.460 | 95.835 | 13.354 | 31.625 | 2.80 R |

(R denotes an observation with a large standardized residual.)

Estimated Regression Coefficients for Hours/Doubling (uncoded units)

| Term | Coef |
| --- | --- |
| Constant | 1322.8425 |
| Rotational Speed (rpm) | −905.2233 |
| Media Volume (ml) | −1.2682 |
| Seeding Density (cells/cm sq) | 0.0036 |
| Days | −269.8567 |
| Rotational Speed (rpm) * Rotational Speed (rpm) | 239.8467 |
| Media Volume (ml) *Media Volume (ml) | 0.0003 |
| Seeding Density (cells/cm sq) * Seeding Density (cells/cm sq) | −0.0000 |
| Days*Days | 17.0229 |
| Rotational Speed (rpm) * Media Volume (ml) | 0.4475 |
| Rotational Speed (rpm) * Seeding Density (cells/cm sq) | 0.0145 |
| Rotational Speed (rpm) *Days | 58.1100 |
| Media Volume (ml) * Seeding Density (cells/cm sq) | 0.0000 |
| Media Volume (ml) *Days | 0.1202 |
| Seeding Density (cells/cm sq) *Days | 0.0003 |

TABLE 6

Response Surface Regression Analysis: Population Doublings versus Rotational Speed, Media Volume, Seeding Density and Days in Culture.

Estimated Regression Coefficients for Doublings (coded units)

| Term | Coef | SE Coef | T | P |
| --- | --- | --- | --- | --- |
| Constant | 2.03667 | 0.15586 | 13.067 | 0.000 |
| Rotational Speed (rpm) | 0.06167 | 0.07793 | 0.791 | 0.444 |
| Media Volume (ml) | 0.14417 | 0.07793 | 1.850 | 0.089 |
| Seeding Density (cells/cm sq) | −0.48500 | 0.07793 | −6.223 | 0.000 |
| Days | 0.15250 | 0.07793 | 1.957 | 0.074 |
| Rotational Speed (rpm) * Rotational Speed (rpm) | −0.25542 | 0.11690 | −2.185 | 0.049 |
| Media Volume (ml) *Media Volume (ml) | −0.03417 | 0.11690 | −0.292 | 0.775 |
| Seeding Density (cells/cm sq) * Seeding Density (cells/cm sq) | 0.47208 | 0.11690 | 4.038 | 0.002 |
| Days*Days | −0.35667 | 0.11690 | −3.051 | 0.010 |
| Rotational Speed (rpm) * Media Volume (ml) | −0.23500 | 0.13498 | −1.741 | 0.107 |
| Rotational Speed (rpm) * Seeding Density (cells/cm sq) | −0.26000 | 0.13498 | −1.926 | 0.078 |
| Rotational Speed (rpm) *Days | −0.17000 | 0.13498 | −1.259 | 0.232 |
| Media Volume (ml) * Seeding Density (cells/cm sq) | −0.09500 | 0.13498 | −0.704 | 0.495 |
| Media Volume (ml) *Days | −0.17750 | 0.13498 | −1.315 | 0.213 |
| Seeding Density (cells/cm sq) *Days | −0.02000 | 0.13498 | −0.148 | 0.885 |

TABLE 6-continued

Response Surface Regression Analysis: Population Doublings versus Rotational Speed, Media Volume, Seeding Density and Days in Culture.

S = 0.2700  R-Sq = 89.5%  R-Sq(adj) = 77.3%

Analysis of Variance for Doublings

| Source | DF | Seq SS | Adj SS | Adj MS | F | P |
|---|---|---|---|---|---|---|
| Regression | 14 | 7.45883 | 7.45883 | 0.532773 | 7.31 | 0.001 |
| Linear | 4 | 3.39682 | 3.39682 | 0.849204 | 11.65 | 0.000 |
| Square | 4 | 3.29139 | 3.29139 | 0.822846 | 11.29 | 0.000 |
| Interaction | 6 | 0.77063 | 0.77063 | 0.128438 | 1.76 | 0.190 |
| Residual Error | 12 | 0.87456 | 0.87456 | 0.072880 | | |
| Lack-of-Fit | 10 | 0.86969 | 0.86969 | 0.086969 | 35.74 | 0.028 |
| Pure Error | 2 | 0.00487 | 0.00487 | 0.002433 | | |
| Total | 26 | 8.33339 | | | | |

Unusual Observations for Doublings

| Obs | StdOrder | Doublings | Fit | SE Fit | Residual | St Resid |
|---|---|---|---|---|---|---|
| 4 | 12 | 1.130 | 1.570 | 0.206 | −0.440 | −2.52 R |

(R denotes an observation with a large standardized residual.)

Estimated Regression Coefficients for Doublings (uncoded units)

| Term | Coef |
|---|---|
| Constant | −20.9241 |
| Rotational Speed (rpm) | 14.0700 |
| Media Volume (ml) | 0.0221 |
| Seeding Density (cells/cm sq) | −0.0003 |
| Days | 5.3308 |
| Rotational Speed (rpm) * Rotational Speed (rpm) | −4.0867 |
| Media Volume (ml) *Media Volume (ml) | −0.0000 |
| Seeding Density (cells/cm sq) * Seeding Density (cells/cm sq) | 0.0000 |
| Days*Days | −0.3567 |
| Rotational Speed (rpm) * Media Volume (ml) | −0.0094 |
| Rotational Speed (rpm) * Seeding Density (cells/cm sq) | −0.0003 |
| Rotational Speed (rpm) *Days | −0.6800 |
| Media Volume (ml) * Seeding Density (cells/cm sq) | −0.0000 |
| Media Volume (ml) *Days | −0.0018 |
| Seeding Density (cells/cm sq) *Days | −0.0000 |

Example 2

Validation of Optimized Culture Conditions

Cells: The cells used were umbilicus-derived cells identified as CBAT 050604B P6 (passage 6).

Media: Dulbecco's Modified Eagle Medium (DMEM)-low glucose, 15% Fetal Bovine Serum, Penicillin-Streptomycin, 2-Mercaptoethanol was used for the validation experiments.

Bottles: The bottles used were 850 cm sq culture bottles (e.g. Corning® catalog number 430851).

Gelatin Coating: Twenty milliliters of 2% gelatin solution were added to each 850 cm sq bottle. The bottles were placed on the roller system for 20 minutes. The gelatin solution was removed by aspiration and each bottle was washed with 20 ml PBS.

Cell Seeding: 5.0E+06 P9 umbilical-derived cells (#050604B) were thawed from a single cryogenic vial and washed to remove DMSO. Cells (2.12E+06) were seeded into a single 850 cm sq roller bottle pre-filled with 300 ml media and pre-gassed for 1 minute with compressed air containing 5% $CO_2$, 95% atmospheric gas.

Incubation: Cells were cultured in a temperature-controlled room set at 37° C.

Speed: 0.7 RPM

Passaging: At passage media was removed from each roller bottle by aspiration and adherent cells were washed with 50 ml PBS. PBS was aspirated and 10 ml of trypsin-EDTA was added. Bottles were returned to the roller system and incubated for 5 minutes at 0.75 RPM. After incubation, 40 ml of media was added to each bottle. The growth medium with cells was then transferred to a 50 ml conical tube and centrifuged for 5 minutes at 300×g. After centrifugation, the media was removed by aspiration and the cell pellet was re-suspended in 10 ml of media. Cells were counted using a Beckman Coulter Cedex® instrument. Cells were seeded into gassed roller bottles at about 2,500 cells/cm sq.

Cell Yield per Passage

TABLE 7

Growth kinetics from Umbilical cell line 050604B expanded from passage six to passage nine under optimized roller bottle culture conditions

| Passage | Seeded | Yield | Expansion | Doubling | Total Doublings | Time (days) | Hours/ Doubling |
|---------|--------|-------|-----------|----------|-----------------|-------------|-----------------|
|         |        | 2.13E+06 | 1      |          |                 |             |                 |
| 6       | 2.13E+06 | 3.10E+07 | 1.46E+01 | 3.87E+00 | 3.87E+00 | 6.00 | 37.24 |
| 7       | 2.13E+06 | 3.55E+07 | 1.67E+01 | 4.06E+00 | 7.93E+00 | 7.00 | 41.36 |
| 8       | 2.13E+06 | 2.54E+07 | 1.20E+01 | 3.58E+00 | 1.15E+01 | 6.00 | 40.23 |
| 9       | 2.13E+06 | 2.56E+07 | 1.20E+01 | 3.59E+00 | 1.51E+01 | 6.00 | 40.10 |

Example 3

Characterization of Cells Expanded on Optimized Culture Conditions

Cells: Cells used for characterization experiments were umbilicus-derived cells at passage 6 (050604B P6)

Growth Medium: Dulbecco's Modified Eagle Medium (DMEM)-low glucose, 15% Fetal Bovine Serum, Penicillin-Streptomycin, 2-Mercaptoethanol was used as the growth medium.

Bottles: 850 cm sq bottles (e.g. Corning® catalog number 430851),

Gelatin Coating: Twenty (20) ml of 2% gelatin solution was added to each 850 cm sq bottle. The bottles were placed on the roller system for 20 minutes. The gelatin solution was removed by aspiration and each bottle was washed with 20 ml PBS.

Cell Seeding: Umbilicus-derived cells at passage 9 (5.0E+06 P9) were thawed from a single cryogenic vial and washed to remove DMSO. Cells (2.12E+06) were seeded into 850 cm sq roller bottles pre-filled with 300 ml media and pre-gassed for 1 minute with compressed air containing 5% $CO_2$, 95% atmospheric gas.

Incubation: Cells were cultured in a temperature-controlled room set at 37° C.

Speed: 0.7 RPM

Cell Harvesting: Media was removed from each roller bottle by aspiration and adherent cells were washed with 50 ml PBS. PBS was removed by aspiration and 10 ml of trypsin-ethylenediaminetetraacetic acid (EDTA) was added. The bottles were incubated for 5 minutes at 0.75 RPM on the roller system. After incubation, 40 ml of media was added to the bottles. Media with cells was then transferred to a 50 ml conical tube and centrifuged for 5 minutes at 300×g. After centrifugation, the media was removed by aspiration and the cell pellet was re-suspended in 10 ml of media. Cells were counted using a Beckman Coulter Cedex® instrument.

Antibody Staining for Flow Cytometry Analysis: Cells were and re-suspended in 3% (v/v) FBS in PBS at a cell concentration of 1×107 per milliliter. Antibody is added as per manufacture's specifications and incubated with cells in the dark for 30 minutes at 4° C. After incubation, cells were washed with PBS and centrifuged to remove unbound antibody. Cells were re-suspended in 500 microliter PBS and analyzed by flow cytometry.

Flow Cytometry Analysis: Flow cytometry analysis was performed with a FACScalibur™ (Becton Dickinson San Jose, Calif.) instrument.

Antibodies: The following antibodies were used:

| Antibody | Manufacture | Catalog Number |
|----------|-------------|----------------|
| CD10 | BD Pharmingen (San Diego, CA) | 555375 |
| CD13 | BD Pharmingen (San Diego, CA) | 555394 |
| CD31 | BD Pharmingen (San Diego, CA) | 555446 |
| CD34 | BD Pharmingen (San Diego, CA) | 555821 |
| CD44 | BD Pharmingen (San Diego, CA) | 555478 |
| CD45RA | BD Pharmingen (San Diego, CA) | 555489 |
| CD73 | BD Pharmingen (San Diego, CA) | 550257 |
| CD90 | BD Pharmingen (San Diego, CA) | 555596 |
| CD117 | BD Biosciences (San Jose, CA) | 340529 |
| CD141 | BD Pharmingen (San Diego, CA) | 559781 |
| PDGFr-alpha | BD Pharmingen (San Diego, CA) | 556002 |
| HLA-A, B, C | BD Pharmingen (San Diego, CA) | 555553 |
| HLA-DR, DP, DQ | BD Pharmingen (San Diego, CA) | 555558 |
| IgG-FITC | Sigma (St. Louis, MO) | F-6522 |
| IgG-PE | Sigma (St. Louis, MO) | P-4685 |

Total RNA Isolation:

RNA was isolated with a RNeasy® Mini Kit according to manufacture's specifications (RNeasy® Mini Kit; Qiagen, Valencia, Calif.). RNA was eluted with 50 μL DEPC-treated water and stored at −80° C.

Reverse Transcription:

RNA was reversed transcribed using random hexamers with the TaqMan™ reverse transcription reagents (Applied Biosystems, Foster City, Calif.) at 25° C. for 10 minutes, 37° C. for 60 minutes and 95° C. for 10 minutes. Samples were stored at −20° C. Genes termed "signature genes" (oxidized LDL receptor, interleukin-8, renin and reticulon), were further investigated using real-time PCR.

Real-Time PCR:

PCR was performed on cDNA samples using Assays-on-Demand™ gene expression products: oxidized LDL receptor (Hs00234028), renin (Hs00166915), reticulon (Hs00382515) CXC ligand 3 (Hs00171061), GCP-2 (Hs00605742) IL-8 (Hs00174103) and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 min and 95° C. for 10 min followed by 40 cycles of 95° C. for 15 sec and 60° C. for 1 min.

Results:

TABLE 6

Expression of cell surface proteins expressed by Umb 050604B cells expanded with static TC flask methods or with the optimized roller bottle method as analyzed by flow cytometry.

| Cell Surface Marker | Static TC Flasks | Roller Bottles |
|---|---|---|
| CD 10 | (+) | (+) |
| CD 13 | (+) | (+) |
| CD 31 | (−) | (−) |
| CD 34 | (−) | (−) |
| CD 44 | (+) | (+) |
| CD 45 | (−) | (−) |
| CD 73 | (+) | (+) |
| CD 90 | (+) | (+) |
| CD 117 | (−) | (−) |
| CD 141 | (−) | (−) |
| PDGFr-alpha | (+) | (+) |
| HLA-ABC | (+) | (+) |
| HLA-DRDPDQ | (−) | (−) |

Real Time PCR Analysis of Cells Expanded in Optimized Roller Bottle Culture Conditions

TABLE 7

Comparison of CT values for genes expressed by cells (Umb 050604B) expanded in static plastic with those grown TC flasks in the optimized roller bottle conditions.

| | CT Values | | | | CT Values-Normalized | | |
|---|---|---|---|---|---|---|---|
| Cell Line | reticulon | LDL-R | IL-8 | GAPDH | reticulon | LDL-R | IL-8 |
| Umb-static culture | 27.79 | 32 | 28.7 | 27.02 | 0.972 | 0.844 | 0.941 |
| Umb -roller bottles | 24.22 | 27.37 | 19.91 | 20.49 | 0.846 | 0.749 | 1.029 |

Example 4

Validation of Optimized Culture Conditions in Cellbind Roller Bottles

Cells:
050604B P7

Media:
Dulbecco's Modified Eagle Medium (DMEM)-low glucose, 15% Fetal Bovine Serum, Penicillin-Streptomycin, 2-Mercaptoethanol.

Bottles:
Corning® 850 cm sq bottles (catalog number 430851), CellBIND® Corning® 850 cm sq bottles (catalog number 3907).

Gelatin Coating:
20 ml of 2% gelatin solution was added to Corning® 850 cm sq bottles (catalog number 430851) and placed on the roller system for 20 minutes. The gelatin solution was removed by aspiration and washed with 20 ml PBS. Cell-BIND® Corning® 850 cm sq bottles are not coated.

Cell Seeding:
5.0E+06 P9 Umbilical 050604B cells were thawed from a single cryogenic vial and washed to remove DMSO. 2.12E+06 cells were seeded into a single 850 cm sq roller bottle pre-filled with 300 ml media and pre-gassed for 1 minute with compressed air containing 5% $CO_2$, 95% atmospheric gas.

Incubation:
Cells were cultured in a temperature controlled room set at 37° C.

Speed:
0.7 RPM

Passage:

At passage media was removed from the roller bottle by aspiration and adherent cells were washed with 50 ml PBS. PBS was aspirated and 10 ml of trypsin-EDTA was added. Bottles were returned to the roller system and incubated for 5 minutes at 0.75 RPM. After incubation 40 ml of media was added to the bottles. Media with cells was then transferred to a 50 ml conical tube and centrifuged for 5 minutes at 300×g. After centrifugation, the media was removed by aspiration and the cell pellet was re-suspended in 10 ml of media. Cells were counted using a Beckman Coulter Cedex® instrument. Cells were seeded into gassed roller bottles at 2,500-cells/cm sq.

Results:

TABLE 8

Actual Cell Yield per Passage for Cells Grown in Gelatin-coated Roller Bottles versus Bottles with CellBIND ® .

| Passage | Seeded | Yield | Date | Expansion | Doubling | Time (days) | Time (hrs) | Hours/ doubling | Harvest Density |
|---|---|---|---|---|---|---|---|---|---|
| Umb050604B Optimal Roller Bottle- Gel Coat | | | | | | | | | |
| 7 | 2.13E+06 | 2.13E+06 | 4-Jan | 1 | | | | | |
| | | 2.45E+07 | 10-Jan | 1.15E+01 | 3.53E+00 | 6.00 | 144.00 | 40.83 | 2.88E+04 |
| Umb050604B Optimal Roller Bottle- CellBIND ® | | | | | | | | | |
| 7 | 2.13E+06 | 2.13E+06 | 4-Jan | 1 | | | | | |
| | | 3.17E+07 | 10-Jan | 1.49E+01 | 3.90E+00 | 6.00 | 144.00 | 36.93 | 3.73E+04 |

The present invention is not limited to the embodiments described and exemplified above, but is capable of variation and modification within the scope of the appended claims.

What is claimed:

1. A method of simultaneously maximizing doubling rate, harvest density, and the total number of population doublings for postpartum cells in a roller bottle culture system comprising:

using a rotational speed from 0.65-0.9 rpm; using at least 300 ml of growth medium in an 850 square centimeter culture bottle;

using a seeding density of less than 2,500 cells per square centimeter; and incubating for between 5.5 to 6.5 days, wherein the postpartum cells that are cultured are characterized as having an identical marker profile as starting cells with respect to each of CD10, CD13, CD44, CD73, CD90, PDGFr-alpha, HLA-ABC, CD31, CD34, CD45, CD117, CD141, and HLA-DRDPDQ, and wherein the postpartum cells are positive for expression of CD10, CD13, CD44, CD73, CD90, PDGFr-alpha, and HLA-ABC, and negative for expression of CD31, CD34, CD45, CD117, CD141, and HLA-DRDPDQ.

2. The method of claim 1 wherein the rotational speed is about 0.7, and the incubation time is about 6 to 6.3 days.

3. The method of claim 1 wherein the rotational speed is about 0.85, and the incubation time is about 6 to 6.3 days.

4. The method of claim 1 wherein a population doubling time is less than about 39 hours, the population achieves at least 3 doublings, and the density of cells at harvest is at least 1.8 E+4 cells per square centimeter.

5. The method of claim 1 wherein the postpartum cells are umbilicus-derived cells.

6. The method of claim 5 wherein the postpartum cells are ATCC Nos PTA-6067 and PTA-6068.

* * * * *